United States Patent
Lockwood et al.

(10) Patent No.: US 11,806,356 B2
(45) Date of Patent: Nov. 7, 2023

(54) COMPOSITIONS AND USES THEREOF FOR TREATMENT OF IDIOPATHIC PRETERM BIRTH

(71) Applicant: UNIVERSITY OF SOUTH FLORIDA, Tampa, FL (US)

(72) Inventors: Charles Lockwood, Tampa, FL (US); Ozlem Guzeloglu-Kayisli, Wesley Chapel, FL (US); Umit Ali Kayisli, Wesley Chapel, FL (US); Frederick Schatz, Tampa, FL (US)

(73) Assignee: University of South Florida, Tampa, FL (US)

( * ) Notice: Subject to any disclaimer, the term of this patent is extended or adjusted under 35 U.S.C. 154(b) by 100 days.

(21) Appl. No.: 17/479,523

(22) Filed: Sep. 20, 2021

(65) Prior Publication Data

US 2022/0088032 A1 Mar. 24, 2022

Related U.S. Application Data

(60) Provisional application No. 63/161,611, filed on Mar. 16, 2021, provisional application No. 63/080,462, filed on Sep. 18, 2020.

(51) Int. Cl.
*A61K 31/557* (2006.01)
*A61K 31/201* (2006.01)
*A61P 15/06* (2006.01)

(52) U.S. Cl.
CPC .......... *A61K 31/557* (2013.01); *A61K 31/201* (2013.01); *A61P 15/06* (2018.01)

(58) Field of Classification Search
CPC ...... A61K 31/201; A61K 31/557; A61P 15/06
See application file for complete search history.

(56) References Cited

U.S. PATENT DOCUMENTS

| | | |
|---|---|---|
| 11,197,868 B2 | 12/2021 | Lockwood |
| 2012/0046261 A1 | 2/2012 | Manuck et al. |
| 2015/0160230 A1 | 6/2015 | Taylor et al. |

FOREIGN PATENT DOCUMENTS

WO WO-2018156945 A1 * 8/2018 .......... A61K 31/436

OTHER PUBLICATIONS

Africander D, Verhoog N, & Hapgood JP (2011) Molecular mechanisms of steroid receptor-mediated actions by synthetic progestins used in HRT and contraception. Steroids 76(7):636-652.

Aung, M.T., Yu, Y., Ferguson, K.K. et al. Prediction and associations of preterm birth and its subtypes with eicosanoid enzymatic pathways and inflammatory markers. Sci Rep 9, 17049 (2019). https://doi.org/10.1038/s41598-019-53448-z.

Baker JD, Ozsan I, Rodriguez Ospina S, Gulick D, & Blair LJ (2018) Hsp90 Heterocomplexes Regulate Steroid Hormone Receptors: From Stress Response to Psychiatric Disease. Int J Mol Sci 20(1).

Bao L, et al. (2007) Decidual prolactin silences the expression of genes detrimental to pregnancy. Endocrinology 148(5):2326-2334.

(Continued)

*Primary Examiner* — Savitha M Rao
(74) *Attorney, Agent, or Firm* — Meunier Carlin & Curfman LLC

(57) ABSTRACT

Disclosed are compositions and methods for delaying or preventing idiopathic preterm birth.

13 Claims, 17 Drawing Sheets

Specification includes a Sequence Listing.

(56) References Cited

OTHER PUBLICATIONS

Binart N, et al. (2000) Rescue of preimplantatory egg development and embryo implantation in prolactin receptor-deficient mice after progesterone administration. Endocrinology 141(7):2691-2697.

Bishop CV (2013) Progesterone inhibition of oxytocin signaling in endometrium. Front Neurosci 7:138.

Blackwell SC, et al. (2020) 17-OHPC to Prevent Recurrent Preterm Birth in Singleton Gestations (Prolong Study): A Multicenter, International, Randomized Double-Blind Trial. Am J Perinatol 37(2):127-136.

Blanks AM & Brosens JJ (2012) Progesterone action in the myometrium and decidua in preterm birth. Facts Views Vis Obgyn 4(3):33-43.

Center MoDPD (2018) 2018 percentage of live births in the U.S. (March of Dimes Perinatal Data Center, https://www.marchofdimes.org/peristats/tools/prematurityprofile.aspx?reg=99).

Chigusa, Yoshitsugu, et al. "Nrf2 activation inhibits effects of thrombin in human amnion cells and thrombin-induced preterm birth in mice." The Journal of Clinical Endocrinology & Metabolism 101.6 (2016): 2612-2621.

Chwalisz K (1994) The use of progesterone antagonists for cervical ripening and as an adjunct to labour and delivery. Hum Reprod 9 Suppl 1:131-161.

Cowchock FS, Reece EA, Balaban D, Branch DW, & Plouffe L (1992) Repeated fetal losses associated with antiphospholipid antibodies: a collaborative randomized trial comparing prednisone with low-dose heparin treatment. Am J Obstet Gynecol 166(5):1318-1323.

Crowther CA, et al. (2017) Vaginal progesterone pessaries for pregnant women with a previous preterm birth to prevent neonatal respiratory distress syndrome (the Progress Study): A multicentre, randomised, placebo-controlled trial. PLoS Med 14(9):e1002390.

Davies TH, Ning YM, & Sanchez ER (2002) A new first step in activation of steroid receptors: hormone-induced switching of FKBP51 and FKBP52 immunophilins. J Biol Chem 277(7):4597-4600.

Denny, Wesley B., et al. "Structure-function analysis of squirrel monkey FK506-binding protein 51, a potent inhibitor of glucocorticoid receptor activity." Endocrinology 146.7 (2005): 3194-3201.

Dodd JM, Jones L, Flenady V, Cincotta R, & Crowther CA (2013) Prenatal administration of progesterone for preventing preterm birth in women considered to be at risk of preterm birth. Cochrane Database Syst Rev (7):CD004947.

Gong S, et al. (2015) Dynamics and correlation of serum cortisol and corticosterone under different physiological or stressful conditions in mice. PLoS One 10(2):e0117503.

Grisha Pirianov, Simon N. Waddington, Tamsin M. Lindström, Vasiliki Terzidou, Huseyin Mehmet, Phillip R. Bennett, The Cyclopentenone 15-Deoxy-Δ12,14-Prostaglandin J2 Delays Lipopolysaccharide-Induced Preterm Delivery and Reduces Mortality in the Newborn Mouse, Endocrinology, vol. 150, Issue 2, Feb. 1, 2009, pp. 699-706, https://doi.org/10.1210/en.2008-1178.

Guzeloglu Kayisli O, et al. (2015) Progestins Upregulate FKBP51 Expression in Human Endometrial Stromal Cells to Induce Functional Progesterone and Glucocorticoid Withdrawal: Implications for Contraceptive-Associated Abnormal Uterine Bleeding. PLoS One 10(10):e0137855.

Guzeloglu-Kayisli O, et al. (2015) Mechanisms of chorioamnionitis-associated preterm birth: interleukin-1beta inhibits progesterone receptor expression in decidual cells. J Pathol 237(4):423-434.

Hahle A, Merz S, Meyners C, & Hausch F (2019) The Many Faces of FKBP51. Biomolecules 9(1).

Herrmann M, et al. (2009) The challenge of continuous exogenous glucocorticoid administration in mice. Steroids 74(2):245-249.

Ho PC (2017) Development of medical termination of pregnancy: a review. BJOG 124(13):1942-1947.

Horseman ND, et al. (1997) Defective mammopoiesis, but normal hematopoiesis, in mice with a targeted disruption of the prolactin gene. EMBO J 16(23):6926-6935.

Hubler TR & Scammell JG (2004) Intronic hormone response elements mediate regulation of FKBP5 by progestins and glucocorticoids. Cell Stress Chaperones 9(3):243-252.

Hubler TR, et al. (2003) The FK506-binding immunophilin FKBP51 is transcriptionally regulated by progestin and attenuates progestin responsiveness. Endocrinology 144(6):2380-2387.

Ishida M, et al. (2007) Reproductive phenotypes in mice with targeted disruption of the 20alpha-hydroxysteroid dehydrogenase gene. J Reprod Dev 53(3):499-508.

Jawerbaum, A., et al. "Influence of peroxisome proliferator-activated receptor γ activation by its endogenous ligand 15-deoxy Δ12, 14 prostaglandin J2 on nitric oxide production in term placental tissues from diabetic women." Molecular Human Reproduction 10.9 (2004): 671-676.

Khan-Dawood FS & Dawood MY (1984) Estrogen and progesterone receptor and hormone levels in human myometrium and placenta in term pregnancy. Am J Obstet Gynecol 150(5 Pt 1):501-505.

Langdown ML & Sugden MC (2001) Enhanced placental GLUT1 and GLUT3 expression in dexamethasone-induced fetal growth retardation. Mol Cell Endocrinol 185(1-2):109-117.

Laskin CA, et al. (1997) Prednisone and aspirin in women with autoantibodies and unexplained recurrent fetal loss. N Engl J Med 337(3):148-153.

Lockwood CJ (2015) Risk factors for preterm birth and new approaches to its early diagnosis. J Perinat Med 43(5):499-501.

Lockwood CJ, et al. (2010) Human labor is associated with reduced decidual cell expression of progesterone, but not glucocorticoid, receptors. J Clin Endocrinol Metab 95(5):2271-2275.

Lockwood CJ, et al. (2012) Abruption-induced preterm delivery is associated with thrombin-mediated functional progesterone withdrawal in decidual cells. Am J Pathol 181(6):2138-2148.

Mahendroo MS, Cala KM, & Russell DW (1996) 5 alpha-reduced androgens play a key role in murine parturition. Mol Endocrinol 10(4):380-392.

Matosin N, Halldorsdottir T, & Binder EB (2018) Understanding the Molecular Mechanisms Underpinning Gene by Environment Interactions in Psychiatric Disorders: The FKBP5 Model. Biol Psychiatry 83(10):821-830.

Mendelson CR (2009) Minireview: fetal-maternal hormonal signaling in pregnancy and labor. Mol Endocrinol 23(7):947-954.

Merlino AA, et al. (2007) Nuclear progesterone receptors in the human pregnancy myometrium: evidence that parturition involves functional progesterone withdrawal mediated by increased expression of progesterone receptor-A. J Clin Endocrinol Metab 92(5):1927-1933.

Mesiano S, et al. (2002) Progesterone withdrawal and estrogen activation in human parturition are coordinated by progesterone receptor A expression in the myometrium. J Clin Endocrinol Metab 87(6):2924-2930.

Mesiano S, Wang Y, & Norwitz ER (2011) Progesterone receptors in the human pregnancy uterus: do they hold the key to birth timing? Reprod Sci 18(1):6-19.

Nadeem L, et al. (2016) Molecular evidence of functional progesterone withdrawal in human myometrium. Nat Commun 7:11565.

Nair SC, et al. (1997) Molecular cloning of human FKBP51 and comparisons of immunophilin interactions with Hsp90 and progesterone receptor. Mol Cell Biol 17(2):594-603.

Norman JE, et al. (2016) Vaginal progesterone prophylaxis for preterm birth (the OPPTIMUM study): a multicentre, randomised, double-blind trial. Lancet 387(10033):2106-2116.

O'Leary JC, 3rd, et al. (2011) A new anti-depressive strategy for the elderly: ablation of FKBP5/FKBP51. PLoS One 6(9):e24840.

Palmsten K, et al. (2019) Oral corticosteroid use during pregnancy and risk of preterm birth. Rheumatology (Oxford). 1262-1271.

Petit E, et al. (2009) Progestins induce catalase activities in breast cancer cells through PRB isoform: correlation with cell growth inhibition. J Steroid Biochem Mol Biol 115(3-5):153-160.

Piekorz RP, Gingras S, Hoffmeyer A, Ihle JN, & Weinstein Y (2005) Regulation of progesterone levels during pregnancy and parturition by signal transducer and activator of transcription 5 and 20alpha-hydroxysteroid dehydrogenase. Mol Endocrinol 19(2):431-440.

Ramo-Fernandez L, et al. (2019) The effects of childhood maltreatment on epigenetic regulation of stress-response associated genes: an intergenerational approach. Sci Rep 9(1):983.

(56) References Cited

OTHER PUBLICATIONS

Ratajczak T, Ward BK, & Minchin RF (2003) Immunophilin chaperones in steroid receptor signalling. Curr Top Med Chem 3(12):1348-1357.
Roizen JD, Asada M, Tong M, Tai HH, & Muglia LJ (2008) Preterm birth without progesterone withdrawal in 15-hydroxyprostaglandin dehydrogenase hypomorphic mice. Mol Endocrinol 22(1):105-112.
Romero R, Dey SK, & Fisher SJ (2014) Preterm labor: one syndrome, many causes. Science 345(6198):760-765.
Rubens CE, et al. (2014) Prevention of preterm birth: harnessing science to address the global epidemic. Sci Transl Med 6(262):262sr265.
Salafia CM, Ghidini A, Lopez-Zeno JA, & Pezzullo JC (1998) Uteroplacental pathology and maternal arterial mean blood pressure in spontaneous prematurity. J Soc Gynecol Investig 5(2):68-71.
Sanchez ER (2012) Chaperoning steroidal physiology: lessons from mouse genetic models of Hsp90 and its cochaperones. Biochim Biophys Acta 1823(3):722-729.
Savouret JF, Misrahi M, & Milgrom E (1990) Molecular action of progesterone. Int J Biochem 22(6):579-594.
Schatz F, et al. (2015) Enhanced Human Decidual Cell-Expressed FKBP51 May Promote Labor-Related Functional Progesterone Withdrawal. Am J Pathol 185(9):2402-2411.
Schmidt MV, Paez-Pereda M, Holsboer F, & Hausch F (2012) The prospect of FKBP51 as a drug target. ChemMedChem 7(8):1351-1359.
Schoen CN, Tabbah S, Iams JD, Caughey AB, & Berghella V (2014) Why the United States preterm birth rate is declining. Am J Obstet Gynecol. 175-180.
Schwartz WJ, 3rd, Christensen HD, Carey JC, Rayburn WF, & Gonzalez C (2003) Systemic administration of betamethasone delays endotoxin-induced preterm labor in the murine model. Am J Obstet Gynecol 188(2):439-443.
Sidibeh CO, et al. (2018) FKBP5 expression in human adipose tissue: potential role in glucose and lipid metabolism, adipogenesis and type 2 diabetes. Endocrine 62(1):116-128.
Smith DF, Baggenstoss BA, Marion TN, & Rimerman RA (1993) Two FKBP-related proteins are associated with progesterone receptor complexes. J Biol Chem 268(24):18365-18371.
Smith DF, Faber LE, & Toft DO (1990) Purification of unactivated progesterone receptor and identification of novel receptor-associated proteins. J Biol Chem 265(7):3996-4003.
Stechschulte LA, et al. (2016) FKBP51 Null Mice Are Resistant to Diet-Induced Obesity and the PPARgamma Agonist Rosiglitazone. Endocrinology 157(10):3888-3900.
Sugimoto Y, et al. (1997) Failure of parturition in mice lacking the prostaglandin F receptor. Science 277(5326):681-683.
Tatro et al., Brain Research, 1286: 1-12 (2009).
Thijssen JH (2005) Progesterone receptors in the human uterus and their possible role in parturition. J Steroid Biochem Mol Biol 97(5):397-400.
Togher, K.L., O'Keeffe, G.W., Khashan, A.S et al. Placental FKBP51 mediates a link between second trimester maternal anxiety and birthweight in female infants. Sci Rep 8, 15151 (2018). https://doi.org/10.1038/s41598-018-33357-3.
Tranguch S, Smith DF, & Dey SK (2007) Progesterone receptor requires a co-chaperone for signalling in uterine biology and implantation. Reprod Biomed Online 14 Spec No. 1:39-48.
Trotnow S, Kniewald T, Al-Hasani S, & Becker H (1981) [Pregnancies obtained by oocyte aspiration, in vitro fertilization, and embryo transfer during clomid/HCG stimulated cycles (author's transl)]. Geburtshilfe Frauenheilkd 41(12):835-836.
Tsai MJ & O'Malley BW (1994) Molecular mechanisms of action of steroid/thyroid receptor superfamily members. Annu Rev Biochem 63:451-486.
Udy GB, et al. (1997) Requirement of STAT5b for sexual dimorphism of body growth rates and liver gene expression. Proc Natl Acad Sci U S A 94(14):7239-7244.
Welsh TN, Hirst JJ, Palliser H, & Zakar T (2014) Progesterone receptor expression declines in the guinea pig uterus during functional progesterone withdrawal and in response to prostaglandins. PLoS One 9(8):e105253.
Williams KC, Renthal NE, Condon JC, Gerard RD, & Mendelson CR (2012) MicroRNA-200a serves a key role in the decline of progesterone receptor function leading to term and preterm labor. Proc Natl Acad Sci U S A 109(19):7529-7534.
Yonkers KA, et al. (2012) Depression and serotonin reuptake inhibitor treatment as risk factors for preterm birth. Epidemiology 23(5):677-685.
Yonkers KA, et al. (2014) Pregnant women with posttraumatic stress disorder and risk of preterm birth. JAMA Psychiatry 71(8):897-904.
Zakar T & Hertelendy F (2007) Progesterone withdrawal: key to parturition. Am J Obstet Gynecol 196(4):289-296.
Zannas AS, et al. (2019) Epigenetic upregulation of FKBP5 by aging and stress contributes to NF-kappaB-driven inflammation and cardiovascular risk. Proc Natl Acad Sci U S A 116(23):11370-11379.
Zannas AS, Wiechmann T, Gassen NC, & Binder EB (2016) Gene-Stress—Epigenetic Regulation of FKBP5: Clinical and Translational Implications. Neuropsychopharmacology 41(1):261-274.

* cited by examiner

CC#1: 15-deoxy-Δ12,14-prostaglandin J2 (15-d-Δ12,14-PGJ2; 11-oxo-prosta-5Z,9,12E,14E-tetraen-1-oic acid; C20H28O3)

CC#2: 10-nitro-9E-octadecenoic acid (10-Nitrooleic Acid, 10-Nitrooleate, 10-nitro-9-trans-Octadecenoic Acid; C18H33NO4).

CC#3: 9-nitro-9E-octadecenoic acid (9-Nitrooleic Acid, 9-Nitrooleate, 9-nitro-9-trans-Octadecenoic Acid; C18H33NO4).

A)

B)

COMPOSITIONS AND USES THEREOF FOR TREATMENT OF IDIOPATHIC PRETERM BIRTH

CROSS-REFERENCE TO RELATED APPLICATIONS

This application claims the benefit of U.S. Provisional Application No. 63/080,462, filed Sep. 18, 2020 and U.S. Provisional Application No. 63/161,611, filed Mar. 16, 2021, which are expressly incorporated herein by reference in their entireties.

INCORPORATION-BY-REFERENCE OF MATERIAL SUBMITTED ELECTRONICALLY

Incorporated by reference in its entirety herein is a computer-readable amino acid sequence listing submitted concurrently herewith and identified as follows: One 4 kilobytes ASCII (Text) file named "11001-123US1_Sequence_Listing.txt," created on Sep. 17, 2021.

FIELD

The present disclosure relates to the field of treatment of idiopathic preterm birth and fetal growth restriction.

BACKGROUND

Preterm birth (PTB), characterized by parturition prior to 37 completed weeks of gestation, has a 5 to 18% prevalence and accounts globally for over 15 million births per year. In 2018, the PTB rate in the U.S. was ~10.0% of livebirths making it the leading cause of perinatal morbidity and mortality. It is also a major cause of childhood lung disease and neurodevelopmental disabilities, contributing to $26 billion/year in health care costs.

Ascending genital tract infections, abruptions, and multiple gestations account for more than half of PTBs. In animal studies, intrauterine or systemic administration of bacteria or bacterial products to pregnant animals leads to preterm delivery and neonatal brain injury. Intrauterine infection can result in proinflammatory cytokine production through the toll-like receptors (e.g., TLR-4) mediated NF-κB activation. Abnormal increase in proinflammatory cytokines can result in preterm labor and antenatal brain injury. It should be understood that delaying preterm birth in the face of overt infection is dangerous for the mother and her fetus.

On the other hand, approximately 45-50% of preterm births are idiopathic, that is they are not associated with inflammation or TLR-NF-κB pathways, abruption, or multifetal gestations. The underlying causes and molecular mechanisms relating to otherwise unexplained or idiopathic PTB remain to be explored however maternal anxiety, depression, and post-traumatic stress as well as fetal stress due to uteroplacental vascular abnormalities have been implicated. The latter also causes fetal growth restriction. What are needed are new compositions and methods for delaying and/or preventing idiopathic PTB and treating fetal growth restriction. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to methods for delaying and preventing idiopathic preterm birth.

The details of one or more embodiments of the invention are set forth in the accompanying drawings and the description below. Other features, objects, and advantages of the invention will be apparent from the description and drawings, and from the claims.

Disclosed herein is a method of delaying and/or preventing idiopathic preterm birth (PTB) in a subject, comprising administering to the subject a therapeutically effective amount of a composition comprising one or more of 15-deoxy-Δ12,14-prostaglandin J2, 9-nitro-9E-octadecenoic acid, 10-nitro-9E-octadecenoic acid or a derivative thereof. In one example, the composition comprises 9-nitro-9E-octadecenoic acid. In one example, the composition comprises 10-nitro-9E-octadecenoic acid. In one example, the composition comprises 15-deoxy-Δ12,14-prostaglandin J2.

In some embodiments, the idiopathic preterm birth is caused by stress, depression, or placental vascular abnormality. In some embodiments, the idiopathic preterm birth is accompanied with stress.

In some embodiments, the composition decreases a level of FKBP51 in a uterine decidual cell. In some embodiments, the composition inhibits glucocorticoid-induced FKBP51 gene expression in a decidual cell. In some embodiments, the composition inhibits an interaction between FKBP51 and progesterone receptor.

In some embodiments, a gestational period of the subject is extended as compared to a control.

Also disclosed herein is a method of delaying or preventing an idiopathic preterm birth in a subject, comprising
a) determining whether a biological sample obtained from the subject has an increased level of FKBP51 as compared to a control; and
b) administering to the subject a therapeutically effective amount of a composition comprising 15-deoxy-Δ12,14-prostaglandin J2, 9-nitro-9E-octadecenoic acid, 10-nitro-9E-octadecenoic acid, or a derivative thereof, or a combination thereof if the biological sample obtained from the subject has an increased level of FKBP51 as compared to the control.

Also disclosed herein is a method of delaying or preventing an idiopathic preterm birth in a subject, comprising
a) determining whether a biological sample obtained from the subject has an altered (increased or decreased) level of 9-nitro-9E-octadecenoic acid and/or 10-nitro-9E-octadecenoic acid as compared to a control; and
b) administering to the subject a therapeutically effective amount of a composition comprising 15-deoxy-Δ12,14-prostaglandin J2 or a derivative thereof if the biological sample obtained from the subject has an altered (increased or decreased) level of 9-nitro-9E-octadecenoic acid or 10-nitro-9E-octadecenoic acid as compared to the control.

In some embodiments, the method further comprises administering to the subject 9-nitro-9E-octadecenoic acid, 10-nitro-9E-octadecenoic acid, or a derivative thereof, or a combination thereof.

Also disclosed herein is a method of treating or preventing fetal growth restriction in a subject, comprising administering to the subject a therapeutically effective amount of a composition comprising 15-deoxy-Δ12,14-prostaglandin J2, 9-nitro-9E-octadecenoic acid, 10-nitro-9E-octadecenoic acid, or a derivative thereof, or a combination thereof.

Also disclosed herein is a method of treating or preventing fetal growth restriction in a subject, comprising
a) determining whether a biological sample obtained from the subject has an increased level of FKBP51 as compared to a control; and
b) administering to the subject a therapeutically effective amount of a composition comprising 15-deoxy-$\Delta$12,14-prostaglandin J2, 9-nitro-9E-octadecenoic acid, 10-nitro-9E-octadecenoic acid, or a derivative thereof, or a combination thereof if the biological sample obtained from the subject has an increased level of FKBP51 as compared to the control.

Also disclosed herein is a method of treating or preventing fetal growth restriction in a subject, comprising
a) determining whether a biological sample obtained from the subject has an altered (increased or decreased) level of 9-nitro-9E-octadecenoic acid and/or 10-nitro-9E-octadecenoic acid as compared to a control; and
b) administering to the subject a therapeutically effective amount of a composition comprising 15-deoxy-$\Delta$12,14-prostaglandin J2 or a derivative thereof if the biological sample obtained from the subject has an altered (increased or decreased) level of 9-nitro-9E-octadecenoic acid and/or 10-nitro-9E-octadecenoic acid as compared to the control.

BRIEF DESCRIPTION OF THE FIGURES

The accompanying figures, which are incorporated in and constitute a part of this specification, illustrate several aspects described below.

FIG. 3A) or CC #2 (WT-ST+CC #2; FIG. 3B) administration. Maternal stress reduces gestational length in WT-ST+Placebo, but not in WT-ST+CC #1 or WT-ST+CC #2 administered mice. Graphs represent 10, 25 and 75 and 90 percentiles with median values.

FIG. 4A) or CC #2 (WT-ST+CC #2; FIG. 4B) administration. Maternal stress-reduced pup birth weight in WT-ST+Placebo are significantly reversed in WT-ST+CC #1 (FIG. 4A) or WT-ST+CC #2 (FIG. 4B), administrated mice. Graphs represent 10, 25, 75 and 90 percentiles with median values.

FIGS. 6A and 6B show decidual mRNA levels of FKBP5 (FIG. 6A) and PGR (FIG. 6B) in placenta accreta (PA, n=7), preeclampsia (PE, n=7), idiopathic preterm birth (iPTB, (n=9) and term specimens (n=10). Data represents mean±SEM; ***P<0.001 vs. PA or PE specimens and *P<0.05 vs. PA or PE specimens by One-Way ANOVA with Dunn's method. (FIG. 6C and FIG. 6D). Double immunostaining for either FKBP51 (FIG. 6C, brown) or PR (FIG. 6D, brown) with vimentin (red) is displayed for decidual cells (DC) at the maternal-fetal interface in PA (n=8), PE (n=8) and iPTB (n=9) specimens. Scale bars: 30 μm. (FIG. 6E and FIG. 6F) HSCOREs for either FKBP51 (FIG. 6E) or PR (FIG. 6F) nuclear immunoreactivity is presented in decidual cells. Bars represent mean±SEM; ***P<0.001 vs. PA or PE specimens by One-Way ANOVA with Student-Newman-Kuels method.

FIG. 7A shows representative images of in situ proximity ligation assay (PLA) in decidua basalis specimens from women with iPTB vs. gestational age (GA)-matched women with indicated PTB due to placenta accreta (PA) or preeclampsia (PE) between 28 to 34 gestational weeks. PLA signals (red) represent the interaction of FKBP51 with PR. DAPI (blue) is used for nuclear staining. Scale bar: 20 μm. FIG. 7B shows higher numbers of PLA signals per cell are detected in iPTB vs. PA or PE. Data represents mean±SEM, n=6/each group; *P<0.05 vs. PA or PE specimens by One-Way ANOVA followed by Student-Newman-Kuels method.

FIG. 8A shows gestational length in Fkbp5$^{+/+}$ and Fkbp5$^{-/-}$ mice mated with either Fkbp5$^{+/+}$ or Fkbp5$^{-/-}$ male mice under non-stress (NST) or stress (ST). Maternal stress reduces gestational length in Fkbp5$^{+/+}$ mated with Fkbp5$^{+/+}$ male, but not in Fkbp5$^{-/-}$ female mated with Fkbp5$^{-/-}$ male mice (n=11/each, except n=13 for Fkbp5$^{-/-}$×Fkbp5$^{-/-}$ mice). Data represent mean±SEM, **P<0.01 in ST-Fkbp5$^{+/+}$ vs. NST-Fkbp5$^{+/+}$ mice with Mann-Whitney U-test; *P<0.05 in ST-Fkbp5$^{-/-}$×Fkbp5$^{+/+}$ male vs. NST-Fkbp5$^{-/-}$×Fkbp5$^{+/+}$ male mice with t-test. P<0.01 in NST-Fkbp5$^{+/+}$ vs. NST-Fkbp5$^{-/-}$× either Fkbp5$^{+/+}$ or Fkbp5$^{-/-}$ male and *P<0.001 in ST-Fkbp5$^{+/+}$ vs. ST-Fkbp5$^{-/-}$× either Fkbp5$^{+/+}$ or Fkbp5$^{-/-}$ male mice with One-Way ANOVA.

FIG. 8B shows serum corticosterone levels in Fkbp5$^{+/+}$ vs. Fkbp5$^{-/-}$ mice at indicated day of gestation under NST or ST conditions. Mean±SEM; n=5/each group; *P<0.001 in ST-Fkbp5$^{+/+}$ vs. NST-Fkbp5$^{+/+}$ at E16 with t-test. *P<0.001 in ST-Fkbp5$^{+/+}$ at E17 or E18 vs. NST-Fkbp5$^{+/+}$ or NST-Fkbp5$^{-/-}$ or ST-Fkbp5$^{-/-}$ mice at E17 or E18 with One Way ANOVA followed by Student-Newman-Keuls test. *P<0.001 in NST-Fkbp5$^{+/+}$ at E17 to E19 vs. NST-Fkbp5$^{-/-}$ mice at E17 to E19 or ST-Fkbp5$^{-/-}$ mice at E18 to E19; *P<0.001 in NST-Fkbp5$^{-/-}$ vs. ST-Fkbp5$^{-/-}$ mice at E17 with One-Way ANOVA followed by Student-Newman-Keuls test. FIG. 8C) or dexamethasone (DEX, n=7; FIG. 8D) administrated Fkbp5$^{+/+}$ or Fkbp5$^{-/-}$ mice. Mean±SEM; P<0.01 vs. CONT-Fkbp5$^{+/+}$ or CORT-Fkbp5$^{+/+}$ (FIG. 8C); and P<0.01 vs. CONT-Fkbp5$^{+/+}$ or DEX-Fkbp5$^{+/+}$ (FIG. 8D) with One-Way ANOVA followed by Student-Newman-Keuls test. CONT: Vehicle (control) administrated mice.

(FIGS. 9A and 9B) Serum progesterone (P4) levels in Fkbp5$^{+/+}$ and Fkbp5$^{-/-}$ mice for either day of gestation (FIG. 9A) or hours prior to delivery (FIG. 9B). Data represent mean±SEM; n=5/each, E16 analyzed by t-test, others by One-Way ANOVA with Student-Newman-Keuls test. (FIG. 9C) Ovarian expression levels of Star and Akr1c18 mRNA in Fkbp5$^{+/+}$ and Fkbp5$^{-/-}$ mice under non-stress (NST) or stress (ST) conditions at E17.25 and E18.25. Mean±SEM; n=4/each, *P<0.05 vs. corresponding Star mRNA levels at E17.25 by t-test. For Akr1c18 mRNA levels at E17.25, *P<0.05 in NST-Fkbp5$^{+/+}$ vs. NST-Fkbp5$^{-/-}$ or ST-Fkbp5$^{-/-}$ and *P<0.05 in ST-Fkbp5$^{+/+}$ vs. NST-Fkbp5$^{+/+}$ or NST-Fkbp5$^{-/-}$ or ST-Fkbp5$^{-/-}$ and *P<0.05 in NST-Fkbp5$^{+/+}$ or ST-Fkbp5$^{+/+}$ vs. NST-Fkbp5$^{-/-}$ or ST-Fkbp5$^{-/-}$ and *P<0.05 in ST-Fkbp5$^{-/-}$ vs. NST-Fkbp5$^{-/-}$ for Akr1c18 mRNA levels at E18.25 with One-Way ANOVA with Student-Newman-Keuls test.

FIG. 10A shows Fkbp5 mRNA expression in uterine tissues from Fkbp5$^{+/+}$ mice under non-stress (NST) or stress (ST) conditions collected at E17.25 and E18.25 as well as E19 for only NST-Fkbp5$^{+/+}$ mice. Data represent mean±SEM; n=5/each; *P<0.05 in ST-Fkbp5$^{+/+}$ vs. corresponding NST-Fkbp5$^{+/+}$ at E17.25 or 18.25 by t-test and P<0.01 at E19 vs. NST-Fkbp5$^{+/+}$ at E17.25 or 18.25 by One Way ANOVA with Student-Newman-Keuls test. Black bars: NST-Fkbp5$^{+/+}$ and grey bars: ST-Fkbp5$^{+/+}$. FIG. 10B shows nuclear FKBP51 immunoreactivity (brown) and HSCORE for FKBP51 expression in decidual cells in NST-Fkbp5$^{+/+}$ vs. ST-Fkbp5$^{+/+}$ mice at E17.25 and 18.25. Mean±SEM; n=6/each; *P<0.001 vs. NST-Fkbp5$^{+/+}$ at E17.25 or 18.25 analyzed by t-test. FIG. 10C shows progesterone receptor (Pgr) mRNA expression in uterine tissues from Fkbp5$^{+/+}$ and Fkbp5$^{-/-}$ mice under NST or ST conditions at E17.25 and E18.25. Mean±SEM; n=4/each. *P<0.05 vs. NST-Fkbp5$^{+/+}$ or NST-Fkbp5$^{-/-}$ at E17.25 and *P<0.05 vs. NST-Fkbp5$^{+/+}$ or NST-Fkbp5$^{-/-}$ or ST-Fkbp5$^{-/-}$ at E18.25 by One Way ANOVA with Student-Newman-Keuls test. FIG. 10D shows representative images of progesterone receptor (PR) immunostaining (brown) in decidual cells and nuclear decidual PR HSCOREs of Fkbp5$^{+/+}$ and Fkbp5$^{-/-}$ mice under NST or ST conditions at E17.25 and 18.25. Mean±SEM; n=6/each. Scale bar: 20 μm. Insert picture represents negative control staining. *P<0.001 in ST-Fkbp5$^{+/+}$ vs. NST-Fkbp5$^{+/+}$ or NST-Fkbp5$^{-/-}$ or ST-Fkbp5$^{-/-}$ and *P<0.001 in NST-Fkbp5$^{+/+}$ vs. NST-Fkbp5$^{-/-}$ or ST-Fkbp5$^{-/-}$ at E17.25; *P<0.001 in ST-Fkbp5$^{+/+}$ vs. NST-Fkbp5$^{+/+}$ or NST-Fkbp5$^{-/-}$ or ST-Fkbp5$^{-/-}$ and *P<0.001 in ST-Fkbp5$^{-/-}$ vs. NST-Fkbp5$^{+/+}$ at E18.25 analyzed by One Way ANOVA with Student-Newman-Keuls test.

FIG. 11A shows Aldo-keto reductase family 1 member C18 (Akr1c18) mRNA expression in uterine tissues from Fkbp5$^{+/+}$ and Fkbp5$^{-/-}$ mice under non-stress (NST) or stress (ST) conditions at E17.25 and E18.25. Bars represent mean±SEM; n=4/each; *P<0.05 vs. NST-Fkbp5$^{+/+}$ or NST-Fkbp5$^{-/-}$ or ST-Fkbp5$^{-/-}$ at E17.25; and *P<0.05 vs. NST-Fkbp5$^{+/+}$ or NST-Fkbp5$^{-/-}$ at E18.25 by One Way ANOVA with Student-Newman-Keuls test. FIG. 11B shows AKR1C18 immunoreactivity (brown) and HSCOREs in decidual cells at E17.25 and 18.25. Inset picture represents negative control staining. Bars represent mean±SEM; n=7/each at E17.25 and n=6/each at E18.25; **P<0.01 vs. NST-Fkbp5$^{+/+}$ or NST-Fkbp5$^{-/-}$ or ST-Fkbp5$^{-/-}$ at E17.25 or E18.25 by One Way ANOVA with Student-Newman-Keuls test. Scale bar: 20 μm.

FIG. 12A shows P4 immunostaining (brown) and nuclear P4 HSCORE levels in decidual cells in Fkbp5$^{+/+}$ and Fkbp5$^{-/-}$ mice under non-stress (NST) or stress (ST) conditions at E17.25 and E18.25. Insert displays negative control staining. Bars represent mean±SEM; n=6/each. *P<0.001 in NST-Fkbp5$^{+/+}$ vs. NST-Fkbp5$^{-/-}$ or ST-Fkbp5$^{-/-}$ and *P<0.001 in ST-Fkbp5$^{+/+}$ vs. NST-Fkbp5$^{+/+}$ or NST-Fkbp5$^{-/-}$ or ST-Fkbp5$^{-/-}$ at E18.25 by One Way ANOVA followed by Student-Newman-Keuls test. Scale bar: 20 μm. FIGS. 12B-12D) Uterine mRNA levels of Stat5b (FIG. 12B) and Prlr (prolactin receptor; FIG. 12C) as well as Oxtr (oxytocin receptor; FIG. 12D) in Fkbp5$^{+/+}$ and Fkbp5$^{-/-}$ mice under NST or ST conditions at E17.25 and E18.25. Bars represent mean±SEM, n=4/each. *P<0.05 in NST-Fkbp5$^{-/-}$ or ST-Fkbp5$^{-/-}$ vs. NST-Fkbp5$^{+/+}$ or ST-Fkbp5$^{+/+}$ at E18.25 by One Way ANOVA with Student-Newman-Keuls test and *P<0.001 at E18.25 vs. corresponding NST-Fkbp5$^{+/+}$ or ST-Fkbp5$^{+/+}$ at E17.25 by t-test (FIG. 12B). P<0.01 at E17.25 vs. their corresponding levels at E18.25 by t-test and *P<0.05 in NST-Fkbp5$^{-/-}$ or ST-Fkbp5$^{-/-}$ vs. NST-Fkbp5$^{+/+}$ or ST-Fkbp5$^{+/+}$ by One Way ANOVA with Student-Newman-Keuls test and (FIG. 12D).

FIG. 14A shows representative pictures of decidual cells, confirmed by vimentin immunofluorescence labeling (green; left panel) in decidua basalis specimens from women with iPTB vs. women with PA or PE. In serial sections, in situ proximity ligation assay (PLA) detected PLA signals (red) which represent the interaction of FKBP51 with PR in middle and right panels [lower and higher magnification, respectively]).

FIG. 14B shows no PLA signal detected in placental villi, which confirms PLA specificity to decidual cells. FIG. 14C shows PLA negative control labelling in decidual cells without adding primary antibodies in decidua basalis. DAPI (blue) used for nuclear staining.

FIG. 16A shows numbers of viable and dead pups in Fkbp5$^{+/+}$ female mated with Fkbp5$^{+/+}$ male mice or Fkbp5$^{+/+}$ female mated with either Fkbp5$^{+/+}$ or Fkbp5$^{-/-}$ male mice. Data represent mean±SEM; n=11/each. FIG. 16B shows graph representing maternal weight gain among all groups between E0 to E18 (n=5/each). FIGS. 16C and 16D show graphs representing residual food (FIG. 16C) and water (FIG. 16D) throughout gestation among the 4 groups, n=5/each; P>0.05 by One Way ANOVA with Student-Newman-Keuls test. NST: non-restrained mice; ST: restrained mice.

FIG. 17A shows that corpus luteal size and appearance are similar in Fkbp5$^{+/+}$ and Fkbp5$^{-/-}$ under non-restraint (NST) and restraint (ST) conditions at E18.25. Scale: 30 µm. FIG. 17B shows similar gene expression levels of Cyp11a1 and Hsd3b2 mRNA in ovaries obtained from Fkbp5$^{+/+}$ and Fkbp5$^{-/-}$ mice under NST or ST conditions at E17.25 and E18.25. Bars represent mean±SEM, n=4/each. P>0.05 by One Way ANOVA with Student-Newman-Keuls test.

FIG. 18A shows significantly higher Akr1c18 mRNA levels in uterine vs. ovarian tissues in either genotype at E17.25. At E18.25, uterine Akr1c18 levels are significantly lower than their corresponding ovarian levels in NST-Fkbp5$^{+/+}$, ST-Fkbp5$^{+/+}$ and ST-Fkbp5$^{-/-}$ mice, whereas uterine Akr1c18 mRNA levels are significantly higher than ovarian levels in NST-Fkbp5$^{-/-}$ mice. Bars represent mean±SEM, n=4/each. ###P<0.001 and ##P<0.01 by paired t-test vs. corresponding ovarian Akr1c18 levels. FIGS. 18B and 18C show comparison of Fkbp4 (FIG. 18B) and steroid 5 alpha-reductase 1 (Srd5a1; FIG. 18C) mRNA expression in uteri from Fkbp5$^{+/+}$ and Fkbp5$^{-/-}$ mice under non-stress (NST) or stress (ST) conditions at E17.25 and E18.25. Bars represent mean±SEM, n=4/each. P>0.05 by One Way ANOVA with Student-Newman-Keuls test.

DETAILED DESCRIPTION

Figure 1:
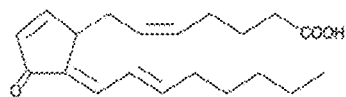
FIG. 1 shows that CC #1, CC #2 and CC #3 inhibits dexamethasone-induced FKBP51 protein levels in decidual cell (DC) monolayers Immunoblot analysis of cell extracts of confluent leukocyte-free term DCs were treated with vehicle (control; Cont), $10^{-7}$ M dexamethasone (Dex) or 15-deoxy-$\Delta$12,14-prostaglandin J2 (CC #1), 10-nitro-9E-octadecenoic acid (CC #2) or 9-nitro-9E-octadecenoic acid (CC #3) or Dex+CC #1, Dex+CC #2 or Dex+CC #3 for 24 h.
Figure 1:
Figure 1:
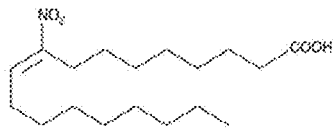
Figure 1:
Figure 1:
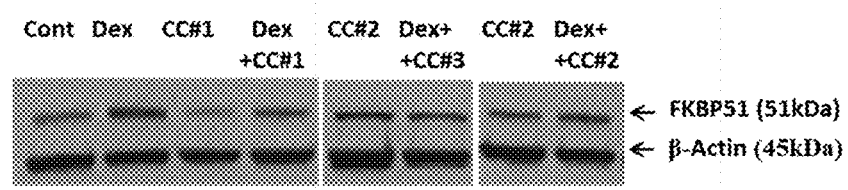

Terms used throughout this application are to be construed with ordinary and typical meaning to those of ordinary skill in the art. However, Applicant desires that the following terms be given the particular definition as defined below.

Terminology

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

As used in the specification and claims, the singular form "a," "an," and "the" include plural references unless the context clearly dictates otherwise. For example, the term "a cell" includes a plurality of cells, including mixtures thereof.

The term "about" as used herein when referring to a measurable value such as an amount, a percentage, and the like, is meant to encompass variations of ±20%, ±10%, ±5%, or ±1% from the measurable value.

"Activate", "activating", and "activation" mean to increase an activity, response, condition, or other biological parameter. This may also include, for example, a 10% increase in the activity, response, "or condition, as compared to the native or control level. Thus, the increase can be a 1, 5, 10, 20, 30, 40, 50, 60, 70, 80, 90, 100%, or any amount of increase in between as compared to native or control levels.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, or via a transdermal patch, and the like. Administration includes self-administration and the administration by another.

The term "biological sample" as used herein means a sample of biological tissue or fluid. Such samples include, but are not limited to, tissue isolated from animals. Biological samples can also include sections of tissues such as biopsy and autopsy samples, frozen sections taken for histologic purposes, peripheral blood mononuclear cell, blood, plasma, serum, sputum, stool, tears, mucus, hair, and skin. Biological samples also include explants and primary and/or transformed cell cultures derived from patient tissues. A biological sample can be provided by removing a sample of cells from an animal, but can also be accomplished by using previously isolated cells (e.g., isolated by another person, at another time, and/or for another purpose), or by performing the methods as disclosed herein in vivo. Archival tissues, such as those having treatment or outcome history can also be used.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a vector, polynucleotide, cells, salts, esters, amides, proagents, active metabolites, isomers, fragments, analogs, and the like.

A "control" is an alternative subject or sample used in an experiment for comparison purposes. A control can be "positive" or "negative."

"Decrease" or "decreased" can refer to any change that results in a lower level of gene expression, protein expression, amount of a symptom, disease, composition, condition, or activity. A substance is also understood to decrease the level of the gene, the protein, the composition, or the amount of the condition when the level of the gene, the protein, the composition, or the amount of the condition is less/lower relative to the output of the level of the gene, the protein, the composition, or the amount of the condition without the substance. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

The term "gene" or "gene sequence" refers to the coding sequence or control sequence, or fragments thereof. A gene may include any combination of coding sequence and control sequence, or fragments thereof. Thus, a "gene" as referred to herein may be all or part of a native gene. A polynucleotide sequence as referred to herein may be used interchangeably with the term "gene", or may include any coding sequence, non-coding sequence or control sequence, fragments thereof, and combinations thereof. The term "gene" or "gene sequence" includes, for example, control sequences upstream of the coding sequence (for example, the ribosome binding site).

The term "gestational period," as used herein, refers to the time period for fetal development from conception until birth. The average gestation period for a variety of mammals is known in the art. Humans, for example, have a gestation period of 40 weeks from a last menstrual period or 38 weeks from conception, while the gestation period for mice is typically about three weeks. The disclosed method desirably "extends" the gestation period of a pregnant mammal if childbirth is not pre- or early-term, i.e., the date of childbirth is full term, late term, or postterm.

The terms "fetal growth restriction" and "intrauterine growth restriction" are synonymous and refer to a condition in which a fetus is smaller than expected for the number of weeks of pregnancy (gestational age). The weight of a fetus is often described in terms of an estimated weight less than the $10^{th}$ percentile. Newborn babies with fetal growth restriction may be called "small for gestational age."

"Increase" can refer to any change that results in a higher level of gene expression, protein expression, amount of a symptom, disease, composition, condition, or activity. A substance is also understood to increase the level of the gene, the protein, the composition, or the amount of the condition when the level of the gene, the protein, the composition, or the amount of the condition is more/higher relative to the output of the level of the gene, the protein, the composition, or the amount of the condition without the substance. Also, for example, an increase can be a change in the symptoms of a disorder such that the symptoms are less than previously observed. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

"Inhibit", "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 1, 5, 10, 20, 30, 40, 50, 60, 70, 80, 90, 100%, or any amount of reduction in between as compared to native or control levels.

"Inhibitors" and "activators" of expression or of activity are used to refer to inhibitory or activating molecules, respectively, identified using in vitro and in vivo assays for expression or activity of a described target protein, e.g., ligands, agonists, antagonists, and their homologs and mimetics. Inhibitors are agents that, e.g., inhibit expression or bind to, partially or totally block stimulation or protease activity, decrease, prevent, delay activation, inactivate, desensitize, or down regulate the activity of the described target protein. Activators are agents that, e.g., induce or activate the expression of a described target protein or bind to, stimulate, increase, open, activate, facilitate, enhance activation or protease inhibitor activity, sensitize, or up regulate the activity of described target protein (or encoding polynucleotide). Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21$^{st}$ Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

With respect to human pregnancies, the terms "preterm birth" (PTB) and "early term birth" are used interchangeably herein and refer to childbirth prior to completion of 37 weeks and between 37 and 39 weeks of pregnancy, respectively. Preterm birth may be further categorized as "late" preterm (i.e., birth between 34 and 36 completed weeks of pregnancy), "moderately" preterm (i.e., birth between 32 and 34 weeks of pregnancy), "very" preterm (i.e., birth at less than 32 weeks of pregnancy), or "extremely" preterm (i.e., birth before 28 weeks of pregnancy). The majority of preterm births occur in the late preterm stage. In contrast, in a "full term" pregnancy, childbirth occurs between 39 and 40 weeks of pregnancy. In a "late term" pregnancy, childbirth occurs during week 41 of pregnancy, and in a "postterm" pregnancy, childbirth occurs at 42 weeks of pregnancy or beyond.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

The term "subject" refers to a human in need of treatment for any purpose, and more preferably a human in need of treatment. The term "subject" can also refer to non-human animals, such as non-human primates.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

"Therapeutically effective amount" or "therapeutically effective dose" of a composition (e.g., a composition comprising an agent) refers to an amount that is effective to achieve a desired therapeutic result. In some embodiments, a desired therapeutic result is the delay and/or prevention of preterm birth. In some embodiments, a desired therapeutic result is the treatment and/or prevention of fetal growth restriction. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Compounds and Methods of Treatment

As discussed above, prior studies have explored the underlying mechanisms related to infection/inflammation-associated PTB using intrauterine injection of lipopolysaccharide (LPS) to activate NF-κB signaling to induce the PTB. Idiopathic preterm birth is not associated with inflammation or TLR-NF-κB pathway. Instead, the present disclosure shows FKBP51 as a main factor regulating idiopathic preterm birth.

The understanding of FKB51 in stress-induced preterm birth remains contradictory. While one earlier study shows that second trimester anxiety decreases birthweight and increases the chance of preterm birth by inhibiting placental FKBP51, another study indicates that FKBP51 knockout animals exhibit prolonged gestation length.

With respect to idiopathic preterm birth, the compositions described herein show the effects on preventing and/or delaying idiopathic preterm birth through an inhibition of FKBP51 expression and/or progesterone receptor (PR)-FKBP51 interactions.

Accordingly, disclosed herein is a method of delaying or preventing idiopathic preterm birth in a subject, comprising administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof.

The term "idiopathic preterm birth" or "spontaneous preterm birth" herein refers to a class of preterm birth that does not arise from a single clearly identifiable etiologic factor, indicative of etiologic heterogeneity. Risk factors include, for example, previous preterm delivery, maternal depression, anxiety and post-traumatic stress disorder, repeated second trimester abortion, abnormal uterus shape, uterine and cervical anomalies, in vitro fertilization, multiple pregnancy, maternal medical complications, gestational bleeding, abnormal placentation, racial origin (e.g. African-American), low socio-economic status, social isolation, smoking and low body mass index before conception. In some embodiments, the idiopathic preterm birth is caused by stress, depression, or placental vascular abnormality. In some embodiments, the idiopathic preterm birth is accompanied with stress. In some embodiments, the subject having idiopathic preterm birth has an increased level of FKBP51 in a biological sample obtained from the subject. In some embodiments, the subject having idiopathic preterm birth has an increased level of 15-deoxy-Δ12,14-prostaglandin J2 in a biological sample obtained from the subject. In some embodiments, the subject having idiopathic preterm birth has an altered (increased or decreased) level of 9-nitro-9E-octadecenoic acid in a biological sample obtained from the subject. In some embodiments, the subject having idiopathic preterm birth has an altered (increased or decreased) level of 10-nitro-9E-octadecenoic acid in a biological sample obtained from the subject. In some embodiments, the subject having idiopathic preterm birth has an increased level of 15-deoxy-Δ12,14-prostaglandin J2, 9-nitro-9E-octadecenoic acid and 10-nitro-9E-octadecenoic acid in a biological sample obtained from the subject. In some embodiments, the subject having idiopathic preterm birth has one or more of the symptoms including, but not limited to, regular or frequent sensations of abdominal tightening (contractions), constant low, dull backache, a sensation of pelvic or lower abdominal pressure, abdominal cramps, and vaginal spotting or light bleeding.

In some embodiments, the composition comprises 9-nitro-9E-octadecenoic acid. In some embodiments, the composition comprises 10-nitro-9E-octadecenoic acid. In some embodiments, the composition comprises 15-deoxy-Δ12,14-prostaglandin J2. In some embodiments, the method comprises administering to the subject a therapeutically effective amount of 15-deoxy-Δ12,14-prostaglandin J2 and 9-nitro-9E-octadecenoic acid. In some embodiments, the method comprises administering to the subject a therapeutically effective amount of 15-deoxy-Δ12,14-prostaglandin J2 and 10-nitro-9E-octadecenoic acid. In some embodiments, the method comprises administering to the subject a therapeutically effective amount of 9-nitro-9E-octadecenoic acid and 10-nitro-9E-octadecenoic acid.

FKBP51 is an Hsp90 co-chaperone that helps regulate the function of specific Hsp90 clients, such as the glucocorticoid receptor (GR) (Denny et al., Endocrinology, 146: 3194-3201 (2005)) and the microtubule-associated protein Tau. The FKBP51 promoter region and introns contain several progesterone or glucocorticoid response elements (PREs or GREs), which mediate transcriptional induction of FKBP51 by progesterone receptor (PR) and/or glucocorticoid receptor (GR) (Hubler T R, Scammell J G., Cell Stress & Chaperones, 9(3): 243-52 (2004)). In turn, elevated levels of FKBP51 can inhibit transcriptional activity of both PR and GR (Hubler et al., Endocrinology, 144(6): 2380-7 (2003); Sanchez, E. R., Biochimica et Biophysica Acta., 1823(3): 722-9 (2012); and Tatro et al., Brain Research, 1286: 1-12 (2009)). It was shown that FKBP51 can also act as a repressor of progesterone receptor (PR) mediated transcription. Further, the present disclosure shows the interaction between FKBP51 and PR in cells (e.g., decidual cells).

"FKBP51" refers herein to a polypeptide that, in humans, is encoded by the FKBP5 gene. In some embodiments, the FKBP51 polypeptide is that identified in one or more publicly available databases as follows: HGNC: 3721, NCBI Entrez Gene: 2289, Ensembl: ENSG00000096060, OMIM®: 602623, UniProtKB/Swiss-Prot: Q13451. In some embodiments, the FKBP51 polypeptide comprises the sequence of SEQ ID NO: 1, or a polypeptide sequence having at or greater than about 80%, about 85%, about 90%, about 95%, or about 98% homology with SEQ ID NO: 1, or a polypeptide comprising a portion of SEQ ID NO: 1. The FKBP51 polypeptide of SEQ ID NO: 1 may represent an immature or pre-processed form of mature FKBP51, and accordingly, included herein are mature or processed portions of the FKBP51 polypeptide in SEQ ID NO: 1.

Accordingly, in some embodiments, the composition disclosed herein inhibits glucocorticoid-induced FKBP51 gene expression in a decidual cell.

In some embodiments, the composition disclosed herein inhibits the interaction between FKBP51 and progesterone receptor.

In some embodiments, the composition disclosed herein decreases a level of FKBP51 in a cell (e.g., a decidual cell). In some embodiments, the decrease is at least about 5% (e.g., at least 10%, at least about 20%, at least about 30%, at least about 40%, at least about 50%, at least about 60%, at least about 70%, at least about 80%, at least about 90%, or at least about 95%) as compared to a cell not administered the composition. In some embodiments, the composition decreases a mRNA level or a protein level of FKBP1 in a cell. In some embodiments, the cell is a decidual cell.

The disclosed methods delay, reduce the likelihood of, and/or desirably prevent preterm birth (PTB) in a pregnant mammal as compared to a mammal not administered the composition. The disclosed methods treat, reduce the likelihood of, and/or desirably prevent fetal growth restriction in a pregnant mammal as compared to a mammal not administered the composition.

Thus, the disclosed methods comprise administering a "therapeutically effective amount" of the composition disclosed herein. A "therapeutically effective amount" refers to an amount effective, at dosages and for periods of time necessary, to achieve a desired therapeutic result (e.g., extension of gestation period, normal fetal growth). A "prophylactically effective amount" refers to an amount effective, at dosages and for periods of time necessary, to achieve a desired prophylactic result (e.g., prevention of preterm birth and/or fetal growth restriction). In some instances, treating fetal growth restriction includes partially or completely reducing the severity of fetal growth restriction (e.g., increases birth weight) as compared with prior to treatment of the subject or as compared with the incidence of such symptom in a study population.

In some embodiments, the gestation period may be extended by at least about 5% (e.g., at least about 10%, at least about 20%, at least about 30%, at least about 40%, at least about 50%, at least about 60%, at least about 70%, at least about 80%, at least about 90%, at least about 100%, or at least about 200%) as compared to a pregnant mammal not administered the composition or as compared with the gestation period in a study population.

Also disclosed herein is a method of delaying or preventing an idiopathic preterm birth in a subject, comprising
a) determining whether a biological sample obtained from the subject has an increased level of FKBP51 as compared to a control; and
b) administering to the subject a therapeutically effective amount of a composition comprising 15-deoxy-Δ12, 14-prostaglandin J2, 9-nitro-9E-octadecenoic acid, 10-nitro-9E-octadecenoic acid or a derivative thereof, or a combination thereof if the biological sample has an increased level of FKBP51 as compared to the control.

In some embodiments, the method further comprises a step of obtaining a biological sample from the subject prior to step a).

Also disclosed herein is a method of delaying or preventing an idiopathic preterm birth in a subject, comprising
a) determining whether a biological sample obtained from the subject has an altered (increased or decreased) level of 9-nitro-9E-octadecenoic acid and/or 10-nitro-9E-octadecenoic acid as compared to a control; and
b) administering to the subject a therapeutically effective amount of a composition comprising 15-deoxy-Δ12, 14-prostaglandin J2 or a derivative thereof, or a combination thereof if the biological sample has an altered (increased or decreased) level of 9-nitro-9E-octadecenoic acid and/or 10-nitro-9E-octadecenoic acid as compared to the control.

In some embodiments, the method further comprises a step of obtaining a biological sample from the subject prior to step a).

In some embodiments, the method comprises administering to the subject a therapeutically effective amount of a composition comprising 15-deoxy-Δ12,14-prostaglandin J2 or a derivative thereof if the biological sample obtained from the subject has an increased level of 9-nitro-9E-octadecenoic acid or 10-nitro-9E-octadecenoic acid as compared to the control. In some embodiments, the method comprises administering to the subject a therapeutically effective amount of a composition comprising 15-deoxy-Δ12,14-prostaglandin J2 or a derivative thereof if the biological sample obtained from the subject has a decreased level of 9-nitro-9E-octadecenoic acid or 10-nitro-9E-octadecenoic acid as compared to the control.

In some embodiments, the biological sample obtained from the subject has a decreased level of 9-nitro-9E-octadecenoic acid or 10-nitro-9E-octadecenoic acid as compared to the control. In some embodiments, the biological sample obtained from the subject has a decreased level of 9-nitro-9E-octadecenoic acid and 10-nitro-9E-octadecenoic acid as compared to the control. In some embodiments, the biological sample obtained from the subject has an increased level of 9-nitro-9E-octadecenoic acid or 10-nitro-9E-octadecenoic acid as compared to the control. In some embodiments, the biological sample obtained from the subject has an increased level of 9-nitro-9E-octadecenoic acid and 10-nitro-9E-octadecenoic acid as compared to the control.

Also disclosed herein is a method of delaying or preventing an idiopathic preterm birth in a subject, comprising
  a) determining whether a biological sample obtained from the subject has an increased level of 15-deoxy-Δ12,14-prostaglandin J2 as compared to a control; and
  b) administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample has an increased level of 15-deoxy-Δ12,14-prostaglandin J2 as compared to the control.

Also disclosed herein is a method of delaying or preventing an idiopathic preterm birth in a subject, comprising
  a) determining whether a biological sample obtained from the subject has an altered (increased or decreased) level of 9-nitro-9E-octadecenoic acid as compared to a control; and
  b) administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample has an altered (increased or decreased) level of 9-nitro-9E-octadecenoic acid as compared to the control.

In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has an increased level of 9-nitro-9E-octadecenoic acid as compared to the control. In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has a decreased level of 9-nitro-9E-octadecenoic acid as compared to the control.

Also disclosed herein is a method of delaying or preventing an idiopathic preterm birth in a subject, comprising
  a) determining whether a biological sample obtained from the subject has an altered (increased or decreased) level of 10-nitro-9E-octadecenoic acid as compared to a control; and
  b) administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample has an altered (increased or decreased) level of 10-nitro-9E-octadecenoic acid as compared to the control.

In some embodiments, the method further comprises a step of obtaining a biological sample from the subject prior to step a).

In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has an increased level of 10-nitro-9E-octadecenoic acid as compared to the control. In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has a decreased level of 10-nitro-9E-octadecenoic acid as compared to the control.

Also disclosed herein is a method of treating or preventing fetal growth restriction in a subject, comprising
  a) determining whether a biological sample obtained from the subject has an increased level of FKBP51 as compared to a control; and
  b) administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample has an increased level of FKBP51 as compared to the control.

In some embodiments, the method further comprises a step of obtaining a biological sample from the subject prior to step a).

Also disclosed herein is a method of treating or preventing fetal growth restriction in a subject, comprising
  a) determining whether a biological sample obtained from the subject has an altered (increased or decreased) level of 9-nitro-9E-octadecenoic acid and/or 10-nitro-9E-octadecenoic acid as compared to a control; and
  b) administering to the subject a therapeutically effective amount of a composition comprising 15-deoxy-Δ12,14-prostaglandin J2 or a derivative thereof, or a combination thereof if the biological sample has an altered (increased or decreased) level of 9-nitro-9E-octadecenoic acid and/or 10-nitro-9E-octadecenoic acid as compared to the control.

In some embodiments, the method further comprises a step of obtaining a biological sample from the subject prior to step a).

In some embodiments, the biological sample obtained from the subject has a decreased level of 9-nitro-9E-octadecenoic acid or 10-nitro-9E-octadecenoic acid as compared to the control. In some embodiments, the biological sample obtained from the subject has a decreased level of 9-nitro-9E-octadecenoic acid and 10-nitro-9E-octadecenoic acid as compared to the control. In some embodiments, the biological sample obtained from the subject has an increased level of 9-nitro-9E-octadecenoic acid or 10-nitro-9E-octadecenoic acid as compared to the control. In some embodiments, the biological sample obtained from the subject has an increased level of 9-nitro-9E-octadecenoic acid and 10-nitro-9E-octadecenoic acid as compared to the control.

In some embodiments, the method comprises administering to the subject a therapeutically effective amount of a composition comprising 15-deoxy-Δ12,14-prostaglandin J2 or a derivative thereof if the biological sample obtained from the subject has an increased level of 9-nitro-9E-octadecenoic acid and/or 10-nitro-9E-octadecenoic acid as compared to the control. In some embodiments, the method comprises administering to the subject a therapeutically effective amount of a composition comprising 15-deoxy-Δ12,14-prostaglandin J2 or a derivative thereof if the biological sample obtained from the subject has a decreased level of 9-nitro-9E-octadecenoic acid and/or 10-nitro-9E-octadecenoic acid as compared to the control.

Also disclosed herein is a method of treating or preventing fetal growth restriction in a subject, comprising
a) determining whether a biological sample obtained from the subject has an increased level of 15-deoxy-Δ12,14-prostaglandin J2 as compared to a control; and
b) administering to the subject a therapeutically effective amount of a composition comprising 15-deoxy-Δ12, 14-prostaglandin J2, 9-nitro-9E-octadecenoic acid, 10-nitro-9E-octadecenoic acid or a derivative thereof, or a combination thereof if the biological sample has an increased level of 15-deoxy-Δ12,14-prostaglandin J2 as compared to the control.

Also disclosed herein is a method of treating or preventing fetal growth restriction in a subject, comprising
a) determining whether a biological sample obtained from the subject has an altered (increased or decreased) level of 9-nitro-9E-octadecenoic acid as compared to a control; and
b) administering to the subject a therapeutically effective amount of a composition comprising 15-deoxy-Δ12, 14-prostaglandin J2, 9-nitro-9E-octadecenoic acid, 10-nitro-9E-octadecenoic acid or a derivative thereof, or a combination thereof if the biological sample has an altered (increased or decreased) level of 9-nitro-9E-octadecenoic acid as compared to the control.

In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has an increased level of 9-nitro-9E-octadecenoic acid as compared to the control. In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has a decreased level of 9-nitro-9E-octadecenoic acid as compared to the control.

Also disclosed herein is a method of treating or preventing fetal growth restriction in a subject, comprising
a) determining whether a biological sample obtained from the subject has an altered (increased or decreased) level of 10-nitro-9E-octadecenoic acid as compared to a control; and
b) administering to the subject a therapeutically effective amount of a composition comprising 15-deoxy-Δ12, 14-prostaglandin J2, 9-nitro-9E-octadecenoic acid, 10-nitro-9E-octadecenoic acid or a derivative thereof, or a combination thereof if the biological sample has an altered (increased or decreased) level of 10-nitro-9E-octadecenoic acid as compared to the control.

In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has an increased level of 9-nitro-9E-octadecenoic acid as compared to the control. In some embodiments, the method comprises administering to the subject a therapeutically effective amount of a composition comprising 15-deoxy-Δ12,14-prostaglandin J2, 9-nitro-9E-octadecenoic acid, 10-nitro-9E-octadecenoic acid or a derivative thereof, or a combination thereof if the biological sample obtained from the subject has a decreased level of 9-nitro-9E-octadecenoic acid as compared to the control.

In some embodiments, the method further comprises a step of obtaining a biological sample from the subject prior to step a).

Fetal growth restriction can begin at any time during pregnancy. It can be tested by fetal ultrasound or doppler ultrasound. Fetal ultrasound tests difference between actual and expected measurements at a certain gestational age. Doppler ultrasound checks the blood flow to the placenta and through the umbilical cord to the fetus. Decreased blood flow (e.g., about 10%, about 20%, about 30%, about 40%, about 50%, about 60%, about 70%, about 80%, about 90%, about 100%, or about 200% as compared to the expected measurements at a certain gestational age) indicates the fetus has FGR. The method or composition disclosed herein can increase the size of fetus at least about 5% (e.g., at least about 10%, at least about 20%, at least about 30%, at least about 40%, at least about 50%, at least about 60%, at least about 70%, at least about 80%, at least about 90%, at least about 100%, or at least about 200%) as compared to the pregnant mammals not administered the composition or as compared with the gestation period in a study population.

In some embodiments, the level of FKBP51 (a level of FKBP5 mRNA and/or a level of FKBP1 protein) may be at least about 5% (e.g., at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, at least about 600%, at least about 700%, at least about 800%, at least about 900%, at least about 1000%, at least about 2000%, at least about 3000%, or at least about 5000%) or at least about 5 times (e.g., at least about 6 times, at least about 7 times, at least about 8 times, at least about 9 times, at least about 10 times, at least about 20 times, at least about 30 times, at least about 40 times, at least about 50 times, or at least about 100 times) higher as compared to a subject in general or a study population.

In some embodiments, the level of 9-nitro-9E-octadecenoic acid may be at least about 5% (e.g., at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, at least about 600%, at least about 700%, at least about 800%, at least about 900%, at least about 1000%, at least about 2000%, at least about 3000%, or at least about 5000%) or at least about 5 times (e.g., at least about 6 times, at least about 7 times, at least about 8 times, at least about 9 times, at least about 10 times, at least about 20 times, at least about 30 times, at least about 40 times, at least about 50 times, or at least about 100 times) higher as compared to a subject in general or a study population.

In some embodiments, the level of 10-nitro-9E-octadecenoic acid may be at least about 5% (e.g., at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, at least about 600%, at least about 700%, at least about 800%, at least about 900%, at least about 1000%, at least about 2000%, at least about 3000%, or at least about 5000%) or at least about 5 times (e.g., at least about 6 times, at least about 7 times, at least about 8 times, at least about 9 times, at least about 10 times, at least about 20 times, at least about 30 times, at least about 40 times, at least about 50 times, or at least about 100 times) higher as compared to a subject in general or a study population.

In some embodiments, the level of 15-deoxy-Δ12,14-prostaglandin J2 may be at least about 5% (e.g., at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, at least about 600%, at least about 700%, at least about 800%, at least about 900%, at least about 1000%, at least about 2000%, at least about 3000%, or at least about 5000%) or at least about 5 times (e.g., at least about 6 times, at least about 7 times, at least about 8 times, at least about 9 times, at least about 10 times, at least about 20 times, at least about 30 times, at least about 40 times, at least about 50 times, or at least about 100 times) higher as compared to a subject in general or a study population.

Methods for determining protein levels are well known in the art, including, for example, immunodetection methods. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods Immunoassays, in their most simple and direct sense, are binding assays involving binding between antibodies and antigen. Many types and formats of immunoassays are known, and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Methods for determining RNA levels are well known in the art, including, for example, PCR, qRT-PCR, arrays, sequencing analysis, RT-LAMP, and isothermal nucleic acid amplification.

Methods for determining 15-deoxy-Δ12,14-prostaglandin J2, 9-nitro-9E-octadecenoic acid, 10-nitro-9E-octadecenoic acid or a derivative thereof are well known in the art, including for example, colorimetric test involving spectrophotometric measurement, high performance liquid chromatography (HPLC), and fluorometric determination, mass spectrometry (MS).

In some embodiments, the method disclosed herein further comprises administering to the subject 9-nitro-9E-octadecenoic acid, 10-nitro-9E-octadecenoic acid or a derivative thereof.

In some embodiments, the composition described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art. In a preferred embodiment, the composition is administered daily via a vaginal route.

The dosage of administration for the composition disclosed herein can be from about 0.01 mg/kg body mass to about 100 mg/kg body mass. In some examples, the dosage is about 0.01 mg/kg body mass, about 0.05 mg/kg body mass, about 0.1 mg/kg body mass, about 0.5 mg/kg body mass, about 1 mg/kg body mass, about 1.5 mg/kg body mass, about 2 mg/kg body mass, about 2.5 mg/kg body mass, about 3 mg/kg body mass, about 3.5 mg/kg body mass, about 4 mg/kg body mass, about 4.5 mg/kg body mass, about 5 mg/kg body mass, about 5.5 mg/kg body mass, about 6 mg/kg body mass, about 6.5 mg/kg body mass, about 7 mg/kg body mass, about 7.5 mg/kg body mass, about 8 mg/kg body mass, about 8.5 mg/kg body mass, about 9 mg/kg body mass, about 9.5 mg/kg body mass, about 10 mg/kg body mass, about 11 mg/kg body mass, about 12 mg/kg body mass, about 13 mg/kg body mass, about 14 mg/kg body mass, about 15 mg/kg body mass, about 20 mg/kg body mass, about 25 mg/kg body mass, about 30 mg/kg body mass, about 35 mg/kg body mass, about 40 mg/kg body mass, about 45 mg/kg body mass, about 50 mg/kg body mass, about 55 mg/kg body mass, about 60 mg/kg body mass, about 65 mg/kg body mass, about 70 mg/kg body mass, about 75 mg/kg body mass, about 80 mg/kg body mass, about 85 mg/kg body mass, about 90 mg/kg body mass, about 95 mg/kg body mass, or about 100 mg/kg body mass. The dosage forms can be adapted for administration by any appropriate route. In some embodiments, the dosage for 15-deoxy-Δ12,14-prostaglandin J2 is about 0.5 mg/kg body mass. In some embodiments, the dosage for 9-nitro-9E-octadecenoic acid is about 0.5 mg/kg body mass. In some embodiments, the dosage for 10-nitro-9E-octadecenoic acid is about 0.5 mg/kg body mass.

The disclosed methods can be performed any time prior to the onset of idiopathic preterm birth or fetal growth restriction. In some aspects, the disclosed methods can be employed 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or 2 weeks prior to the onset of idiopathic preterm birth or fetal growth restriction or a symptom thereof. Preferably, the composition disclosed herein is administered beginning about the $18^{th}$ to $22^{nd}$ week of gestation until about the $37^{th}$ week of gestation, or for approximately 14 to 19 weeks, depending on the gestational age at the beginning of treatment and the date of delivery. In some embodiments, the composition disclosed herein is administered beginning about the $16^{th}$ week of gestation until about the $37^{th}$ week of gestation, or for approximately 21 weeks. In some embodiments, the composition disclosed herein is administered beginning about the time of a positive pregnancy test until about the $37^{th}$ week of gestation or beginning about the 2nd to 4th week of gestation, for approximately 33 to 35 weeks.

Dosing frequency for the composition disclosed herein, includes, but is not limited to, at least once every month, once every three weeks, once every two weeks, once a week, twice a week, three times a week, four times a week, five times a week, six times a week, or daily, twice a day, three times a day, four times a day, or five times a day. In some embodiments, the interval between each administration is less than about less than about a month, less than about 3 weeks, less than about 2 weeks, or less than less than about a week, such as less than about any of 6, 5, 4, 3, 2, or 1 day. In some embodiments, the dosing frequency for the composition includes, but is not limited to, at least once a day, twice a day, or three times a day. In some embodiments, the interval between each administration is less than about 48 hours, 36 hours, 24 hours, 22 hours, 20 hours, 18 hours, 16 hours, 14 hours, 12 hours, 10 hours, 9 hours, 8 hours, or 7 hours. In some embodiment, the interval between each administration is less than about 24 hours, 22 hours, 20 hours, 18 hours, 16 hours, 14 hours, 12 hours, 10 hours, 9 hours, 8 hours, 7 hours, or 6 hours. In some embodiment, the interval between each administration is constant. For example, the administration can be carried out daily, every two days, every three days, every four days, every five days, or weekly. Administration can also be continuous and adjusted to maintaining a level of the compound within any desired and specified range.

The composition is preferably administered to a pregnant mammal at risk for PTB, but without evidence of infection (fever, uterine tenderness, elevated white blood cell count) or abruption (vaginal bleeding, uterine tachysystole, hypofibrinogenemia) beginning as early as the onset of gestation or when the cervix is reduced in length for that point in gestation (e.g., less than 2 cm in women less than 37 weeks gestation) or there is evidence of fetal fibronectin in cervicovaginal secretions between 22 and 37 weeks gestation. More preferably, the composition is administered to a pregnant mammal beginning as early as the onset of gestation and whose cervix has a length is at least about 1.0 cm and at most about 8.0 cm, and even more preferably, the composition is administered to a pregnant mammal whose cervix has a length less than or equal to 3.0 cm or less than or equal to 2.5 cm in more preferable embodiments.

EXAMPLES

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or be able to ascertain using no more than routine experimentation, many equivalents to the specific embodiments of the invention described herein. While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Study Approval. Collection of placental specimens was approved by the University of South Florida Institutional Review Board (#19472). Written informed consent was received from patients prior to inclusion in the study and patients were de-identified. Breeding and all experimental procedures were conducted with prior approval of the Animal Care and Use Committee at the University of South Florida (USF #2235R and #3063M).

Collection of Human Tissues. Placental specimens containing decidua basalis were obtained from patients with idiopathic PTB (iPTB, n=9) or from patients undergoing cesarean delivery in the absence of labor due to preeclampsia (PE, n=8) or placenta accreta (PA, n=8) or from term placentas after the onset of labor (n=10). The decidua basalis was obtained by dissecting basal plate from cotyledons of the placenta, and by trimming excess villous tissues. Collected tissues were rinsed with PBS to remove blood. iPTB specimens displayed no clinical or histological evidence of either abruption or chorioamnionitis. Placental specimens obtained from patients with PE or PA served as gestational age (GA)-matched controls. The GA for iPTB specimens (Mean±SEM; 31.54±0.74 weeks) did not significantly differ from that of control PE or PA patients (31.10±0.88 or 33.22±0.31 weeks, respectively, P=0.32).

Animals. Female and male $Fkbp5^{+/-}$ breeders, a mixed C57BL/6-129/SvJ background (kindly gifted by the late Dr. Chad Dickey, Byrd Alzheimer's Research Institute, University of South Florida) were house-mated to generate $Fkbp5^{+/+}$ and $Fkbp5^{-/-}$ littermates. Mice were housed in a temperature-controlled environment with 12-h light/dark cycles with ad libitum access to food and water.

Timing of Labor in $Fkbp5^{+/+}$ and $Fkbp5^{-/-}$ Mice. To examine the effect of deletion of the Fkbp5 gene on birth timing, female $Fkbp5^{+/+}$ and $Fkbp5^{-/-}$ mice (6-8 weeks-old) were mated with an adult $Fkbp5^{+/+}$ male (12-16 weeks old) by housing 1:1 for 4 h (9.00 am-1.00 pm). Pregnancy was confirmed by the presence of a vaginal plug or sperm in vaginal smears; gestational day (E) was designated at that time (10.00 am) as 0 dpc of pregnancy. The timing of delivery was monitored from E18 through E21 by observing mice every 4 h upon completion of delivery, and gestational length was calculated. Litter size, numbers of live and dead pups were recorded. Additionally, to determine whether there was a relative contribution of fetal genotype on birth timing, female $Fkbp5^{-/-}$ mice were also mated with an adult male $Fkbp5^{-/-}$ mice as described above and timing of labor was recorded.

Experimental Procedures. Time-mated pregnant Fkbp5$^{+/+}$ and Fkbp5$^{-/-}$ mice (n=11) were randomly assigned into non-restraint stress (NST-) and restraint stress (ST) groups. Restraint stress was administered in three sessions for 1 h using standard restraint chambers (1.5"×4"; Braintree Scientific, Inc., Braintree, MA) starting on E8 through 18, while the control group was left undisturbed during the whole pregnancy. This time frame was chosen to eliminate the potential impact of maternal stress on implantation and on neuronal development. The stress schedule was varied day to day to reduce a possible habituation to restraint stress. Pregnant mice were weighed every three days and water/food intake were measured weekly.

Maternal Dexamethasone or Corticosterone injection. Dexamethasone-21-phosphate disodium salt (DEX; Sigma-Aldrich, St. Louis, MO) suspended in sterile PBS was administered intraperitoneally at 200 µg/kg. Corticosterone (CORT; Sigma-Aldrich) was dissolved in ethyl alcohol and diluted in PBS before injection and administered subcutaneously at 10 mg/kg. The drugs were administered daily to time-mated Fkbp5$^{+/+}$ and Fkbp5$^{-/-}$ mice× Fkbp5$^{+/+}$ male mice DEX (n=7) or corresponding vehicle control (PBS; n=7) as well as CORT (n=6) or corresponding vehicle control (0.5% ethanol; n=6) starting E8 through E18.

Monitoring Body Weight, Food and Water Intake. The pregnant female mice were weighed every three days starting at E0 to 18 to determine whether Fkbp5 gene deficiency or maternal restraint stress influenced gestational weight gain. Weight gain was determined by body weight measurement after E0. Also, to determine whether restraint stress affects food/water intake, the amount of food and water were measured every week by weighing food and water placed in the cage at E0 and subtracting the weight of residual food and water at E18. The cage floor was checked to ensure any spilled food pellets were collected and measured as well.

Blood Sample Collection. Blood samples (n=5/each; ~200 µl) from either unrestrained- or restrained-Fkbp5$^{+/+}$ or Fkbp5$^{-/-}$ mice were obtained with microhematocrit tubes by retro-orbital phlebotomy after anesthetization: 1) on E11 after the first stress exposure between 9:00 to 11:00 am to measure the levels of cortisol and corticosterone in order to confirm that pregnant mice were responding to the stress conditions; and 2) daily from E16 to E20 to measure serum corticosterone and P4 levels. Serum was separated by centrifugation and stored at −80° C. until hormone measurements.

Measurements of Corticosterone and Progesterone Levels. Serum cortisol and P4 levels were measured using EIA kits (R&D Systems, Minneapolis, MN) while corticosterone was measured using EIA kits from BioVendor (Ashville, NC), all according to the manufacturers' protocol.

Mice Tissue Collection. Animals were euthanized and uterine and ovarian tissues collected from timed-pregnant unrestrained and restrained Fkbp5$^{+/+}$ and Fkbp5$^{-/-}$ mice at E17.25 and 18.25 as well as at E19 from unrestrained Fkbp5$^{+/+}$ mice. Under dissection microscopy, uterine tissues containing myometrial and endometrial tissues were carefully collected after removal of all fetal tissues and stored for RNA studies. Placental tissues including decidua and myometrium were collected and processed for paraffin embedding for histochemical and immunohistochemical studies to evaluate relevant protein expression in different maternal and fetal tissue compartments. Ovaries were dissociated from surrounding fat and oviduct. In each mouse, one ovary was used for RNA studies, whereas the other ovary was used for paraffin embedding. All collected tissues were rinsed in PBS and stored at −80° C. until analysis.

RNA Isolation and Reverse Transcription. Total RNA obtained from decidua basalis of patients with term labor (n=10) or experiencing iPTB (n=9) or PE (n=7) or PA (n=7) as well as collected murine tissues were extracted using RNAeasy Mini Kit (Qiagen, Valencia, CA) according to the manufacturer's protocol. After DNAse treatment (Qiagen), 500 nanogram of total RNA from each sample was reverse transcribed using the Qmniscript Kit (Qiagen) according to the manufacturer's instructions.

Quantitative Real Time-PCR (qPCR). qPCR was performed on both human and murine tissues to quantify the expression of several genes presented in Tables 1A and 1B, respectively using TaqMan gene expression arrays (Applied Biosystems, Foster City, CA) on ABI 7500 thermocycler instrument. All samples were run in duplicate and the average was used for each sample. The cycling conditions were 95° C. for 10 minutes, followed by 45 cycles of 95° C. for 15 second and 60° C. for 1 minute. As a negative control, water was substituted for cDNA. Quantification data for the genes of interest are expressed relative to β-actin gene as an internal control. The $2^{-\Delta\Delta Ct}$ (cycle threshold) method was used to calculate relative expression levels. Data were normalized to expression levels of each gene in NST-Fkbp5$^{+/+}$ mice on E17.25 and results are reported as fold-change in gene expression levels among the different groups.

Tables 1A and 1B. Detailed description of primers used for real-time quantitative PCR for human (1A) and mice (1B).

TABLE 1A

| Primer/Probe name | Taqman Assay ID |
| --- | --- |
| FKBP5 | Hs01561006_m1 |
| PGR | Hs01556702_m1 |
| PGR-B | Hs04419616_s1 |
| β-Actin | Hs99999903_m1 |

TABLE 1B

| Primer/Probe name | Taqman Assay ID |
| --- | --- |
| Fkbp5 | Mm00487406_m1 |
| Pgr | Mm00435628_m1 |
| Akr1c18 | Mm00506289_m1 |
| Stat5b | Mm00839889_m1 |
| Prlr | Mm04336676_m1 |
| Oxtr | Mm01182684_m1 |
| Star | Mm00441558_m1 |
| Cyp11a1 | Mm00490735_m1 |
| Hsd3b2 | Mm00462685_m1 |
| Fkbp4 | Mm00487391_m1 |
| Srd5a1 | Mm00614213_m1 |
| β-Actin | Mm00607939_s1 |

Histomorphometric Analyses of Ovaries. Ovaries obtained from unrestrained and restrained Fkbp5$^{+/+}$ or Fkbp5$^{-/-}$ mice at 18.25 (n=4/each) were fixed in 4% paraformaldehyde (PFA) solution for 18 hours at room temperature and embedded in paraffin. The serial 5 µm sections from each ovary were cut and stained by the Hematoxylin & Eosin (H&E, Sigma-Aldrich). Slides were examined under an Axio Imager II microscope (Zeiss; White Plains, NY) using ZEN 2011 software.

Immunohistochemistry and HSCORE Analysis Immunostaining was performed on 4% PFA-fixed, paraffin-embedded sections from GA-matched iPTB (n=9) and PE (n=8) and PA-complicated (n=8) pregnancies as well as mouse ovarian and uterine samples. As previously described deparaffinization, antigen retrieval using citrate buffer (pH: 6.0) and endogenous peroxidase quenching in 3% hydrogen peroxide solution was performed. Following washing steps with PBS, slides were incubated with 5% normal goat or horse serum (Vector Labs, Burlingame, CA) for blocking and then with the primary antibodies presented in Table 2 either overnight or at room temperature. After washing, the slides were incubated with biotinylated secondary antibodies (Vector Labs) for 30 minutes, then incubated with streptavidin-conjugated peroxidase complex (Vector Labs) for 30 minutes. Following several rinses with TBS-T, immunoreactivity was developed using diaminobenzidine (DAB; 3, 3-diaminobenzidine tetrahydrochloride dihydrate; Vector Labs) as the chromogen, and sections were counterstained with hematoxylin.

TABLE 2

List of primary and secondary antibodies used in this study. Detailed description of antibodies that used for immunohistochemistry (IHC), immunofluorescence (IF) and Proximity ligation assay (PLA).

| Antibody Name | Catalog number and Company | Species | Dilution used for |
|---|---|---|---|
| FKBP51 | R&D, AF4094 | Goat | IHC; 1:1500 (for human) |
|  |  |  | IHC; 1:1000 (for mice) |
|  |  |  | PLA; 1:800 (for human) |
| Progesterone receptor | Dako, M3568 | Mouse | IHC; 1:100 (for human) |
|  | Thermo Scientific, MA1-410 | Mouse | IHC; 1:600 (for mice) |
|  | Cell Signaling, 8757 | Rabbit | PLA; 1:100 (for human) |
| Akr1c18 | Kerafest, EB4002 | Rabbit | IHC; 1:6000 (for mice) |
| Progesterone (P4) | Bio-Rad, 7720-0496 | Rabbit | IHC; 1:200 (for mice) |
| Vimentin | Abcam, ab39376 | Chicken | IHC; 1:400 (for human) |
|  |  |  | IF; 1:300 (for human) |
| Alexa Fluor-488 labeled anti-chicken | Invitrogen, A-11039 | Goat | IF; 1:2000 |
| Biotinylated anti-mouse | Vector, BA-2000 | Horse | IHC; 1:400 |
| Biotinylated anti-goat | Vector, BA-9500 | Horse | IHC; 1:400 |
| Biotinylated anti-chicken | Jackson Imm., 703-065-155 | Donkey | IHC; 1:1000 |

To identify decidual cells, human tissues were double immunostained sequentially with vimentin (a decidual marker, Abcam, Cambridge, MA), as described above. Vector RED (Vector Labs) was used as chromogens. For negative control, appropriate non-specific IgG isotype was used at the same concentrations as the primary antibody Immunoreactivity for each antibody was assessed by histological score (HSCORE) analysis, a semi-quantitative method that evaluates the intensity and the number of immunostained cells by two blinded investigators as described.

In Situ Proximity Ligation Assays. Duolink II in situ Proximity Ligation assays (PLA) detection kit (Sigma-Aldrich) was used to detect the interaction between FKBP51 and PR. 4% PFA fixed paraffin-embedded decidua basalis specimens from women with iPTB (n=6) vs. GA-matched control PA or PE (n=6/each) were deparaffinized and rehydrated, then, antigen retrieval was carried out by incubating the slides in citrate buffer (pH=6.0) in microwave for 20 min. After washing steps, the slides were incubated with blocking solution for 1 hour at 37° C. and then incubated with primary antibodies (PR rabbit monoclonal antibody; Cell Signaling, Danvers, MA) and FKBP51 goat polyclonal antibody; R&D Systems) for overnight at +4° C. Primary antibodies were carefully selected from different species sources based on negligible background. Hybridization with anti-rabbit MINUS and goat PLUS PLA probes, ligation and amplification of conjugants were performed as per the manufacturer's instructions. Negative controls were included in all experiments in the absence of primary antibodies. Slides were mounted with in situ mounting medium with DAPI (Sigma-Aldrich). Ten different areas were randomly selected per slide, and photographs were obtained with 40× or 100× magnification and image were analyzed using a Zeiss fluorescence microscope with ZEN 2012 software system. The interaction of FKBP51 with PR was calculated as the number of PLA positive dots per cell.

Statistics. Normality of data were investigated using the Kolmogorov-Smirnov test. Results that were normally distributed were analyzed by t-test or One-Way ANOVA, whereas data not normally distributed were analyzed by Mann-Whitney U or Kruskal-Wallis test followed by Student-Newman-Keuls or Dunn's test. Analyses were performed using SigmaStat version 3.0 (Systat Software, San Jose, CA); *$P<0.05$, $P<0.01$ or *$P<0.001$ were considered statistically significant.

Example 1. In Vitro Approaches for Inhibition of FBPK51 Expression Levels in Decidual Cell Cultures Three endogenous biochemicals (CC #1, CC #2, CC #3), which exist in human blood/tissues were tested as potential inhibitors of FKBP51 expression/action and confirmed that dexamethasone-induced inhibits FKBP51 expression in decidual cell cultures by all three compounds (FIG. 1).

Figure 2:
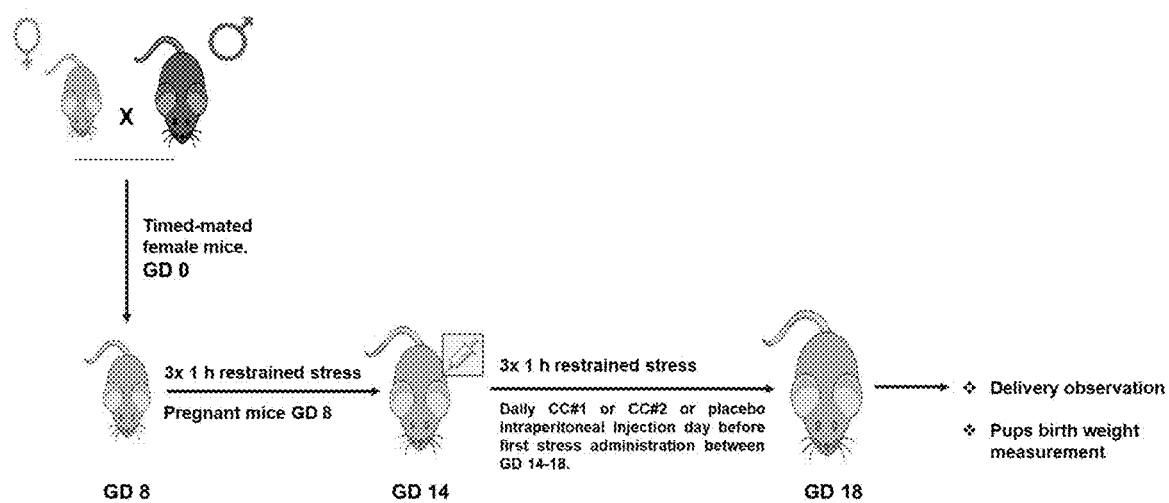
FIG. 2 shows experimental design to test effects of CC #1 and CC #2 administration in maternal stress induced pregnant mice. Wild-type adult female mice were mated with adult males by housing 1:1 for 4 h (9.00 am-1.00 pm). Pregnancy was confirmed by observing vaginal plug and the presence of sperm in vaginal smears, which was designated as gestation day (GD) 0 dpc (10.00 am). Time-mated pregnant mice were randomly assigned into non-stress or restraint stress (ST) groups. Restraint stress was administered in three sessions for 1 h using standard restraint chambers starting on GD 8 through GD 18, while the control group was left undisturbed during pregnancy. Before first restrained stress administration, daily intraperitoneal injection of CC #1 (0.5 mg/kg) or CC #2 (0.5 mg/kg) or placebo (PBS) was administered in ST-mice from GD14 to GD 18. The timing of delivery was monitored. Pups weight, litter size, numbers of live and dead pups were recorded.

Example 2. In Vivo Therapeutic Impacts of FBPK51 Inhibitors CC #1 and CC #2 on Maternal Stress-Induced Preterm Birth (PTB) and Fetal Growth Restriction (FGR) in WT Mice Experimental design to test effects of CC #1 and CC #2 administration in maternal stress induced pregnant mice (FIG. 2). Wild-type adult female mice were mated with adult males by housing 1:1 for 4 h (9.00 am-1.00 pm). Pregnancy was confirmed by observing vaginal plug and the presence of sperm in vaginal smears, which was designated as gestation day (GD) 0 dpc (10.00 am). Time-mated pregnant mice were randomly assigned into non-stress or restraint stress (ST) groups. Restraint stress was performed in three sessions for 1 h using standard restraint chambers starting on GD 8 through GD 18, while the control group was left undisturbed during pregnancy. Before first restrained stress administration, daily intraperitoneal (I.P.) injection of CC #1 (0.5 mg/kg) or CC #2 (0.5 mg/kg) or placebo (PBS) was administered in ST-mice from GD14 to GD 18. The timing of delivery was monitored. Pups weight, litter size, numbers of live and dead pups were recorded.

Figure 3A:
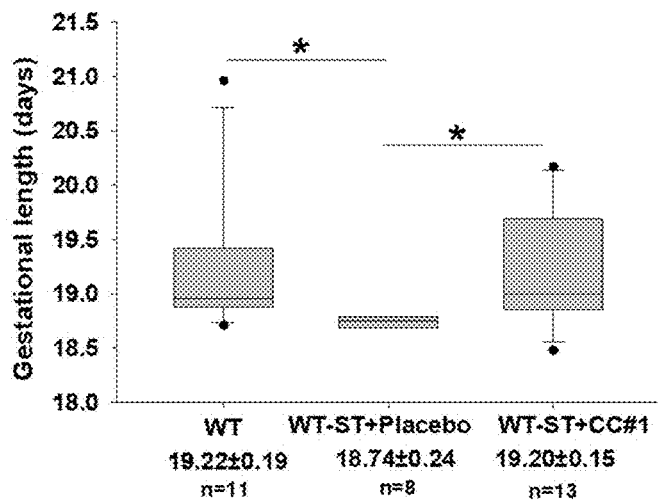
FIGS. 3A-3B show that administration of CC #1 and CC #2 reverses maternal stress induced preterm birth (PTB) in wild-type mice. Gestational length in mice under non-stress (WT) or stress (WT-ST) plus either placebo (WT-ST+Placebo) or CC #1 (WT-ST+CC #1.
Figure 3B:
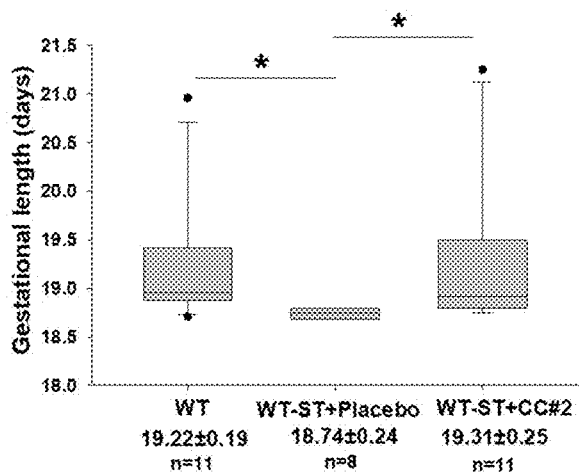
Figure 4A:
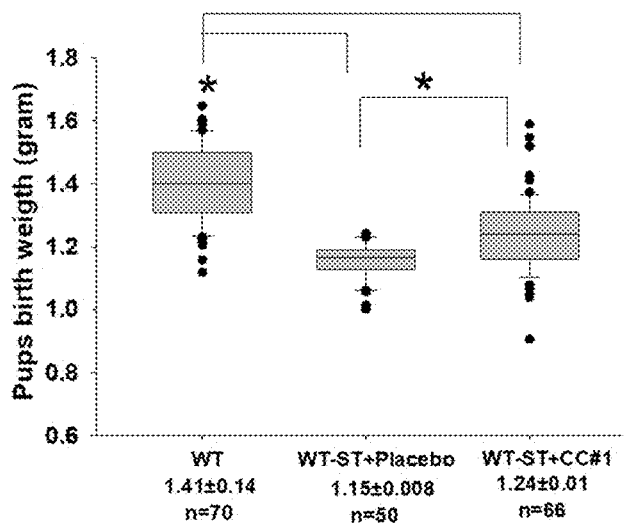
FIGS. 4A-4B show that administration of CC #1 and CC #2 prevents maternal stress induced fetal growth restriction (FGR) in wild-type mice. Pubs birth weight in mice under non-stress (WT) or stress (WT-ST) plus either placebo (WT-ST+Placebo) or CC #1 (WT-ST+CC #1.
Figure 4B:
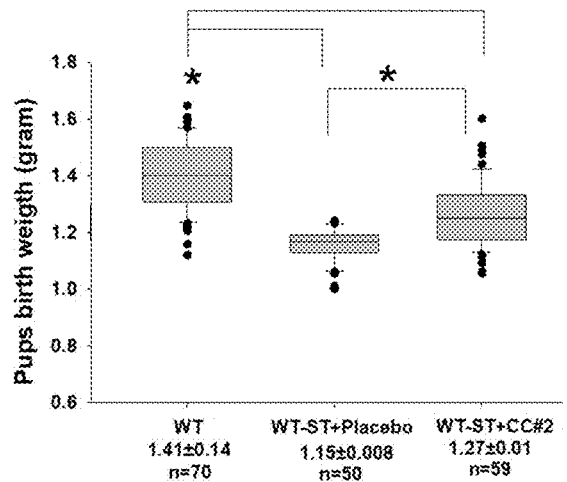
Figure 5A:
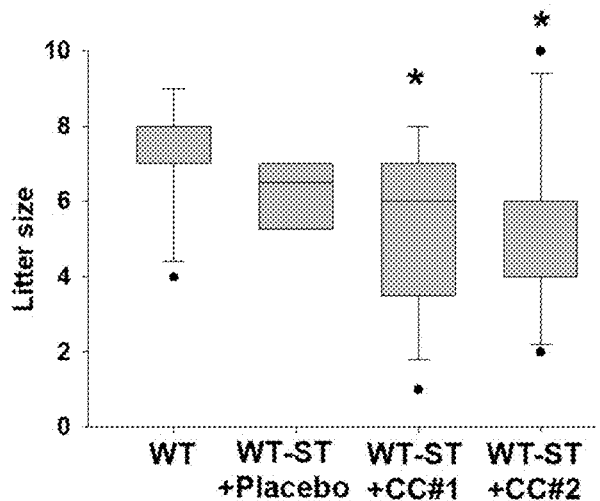
FIGS. 5A-5B show that CC #1 or CC #2 administration did not affect litter size in maternal stress induced mice. Numbers of viable and dead pups in WT or ST+placebo or CC #1 or CC #2 administrated mice. Graphs represents litter size (FIG. 5A) and dead pups at birth (FIG. 5B) among groups. *P<0.05 vs. WT. Graphs represent 10, 25, 75 and 90th percentiles with median values (FIG. 5A) or Mean±SEM (FIG. 5B).
Figure 5B:
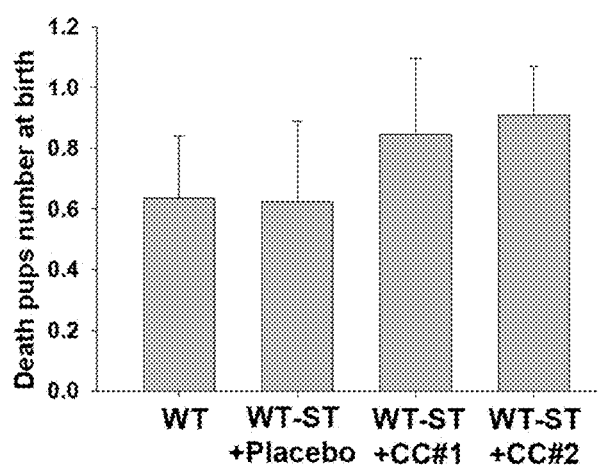

FIGS. 3A-3B show that both CC #1 (FIG. 3A) and CC #2 (FIG. 3B) prevent maternal stress induced PTB in mice. And FIGS. 4A-4B show that CC #1 (FIG. 4A) and CC #2 (FIG. 4B) prevent maternal stress induced FGR in mice. Further, data in FIGS. 5A-5B indicate that CC #1 (FIG. 5A) or CC #2 (FIG. 5B) administration did not affect litter size in maternal stress administered mice.

Synthetically modified versions of these compounds (FIG. 1) are developed. Besides their common effects to inhibit FKBP51 expression and prevent PTB and FGR, these three fatty acid derivatives have similar core structures. Therefore, the current results indicate that the design of new chemical modifications of any of the three compounds can have therapeutic actions to prevent both PTB and FGR. The nitro group is a common feature of 9-nitro oleic acid and 10-nitro oleic acid, but not in 15-deoxy-12,14-prostaglandin J2. Moreover, the C=C double bonds at the 5-, 12- and 14-positions and 11-oxo group are present in 15-deoxy-12,14-prostaglandin J2, but not in 9-nitro oleic acid and 10-nitro oleic acid. Therefore, further synthetic modifications of these compounds including, but not limited to the addition, removal or rearrangements of the oxo groups and/or nitro groups in their chemical formula can enhance their therapeutic potentials against PTB and FGR. There is a great therapeutic effect for PTB and FGR by numerous other synthetic modifications such as acetylation, hydroxylation within or with an expanding chemical framework of 9-nitro oleic acid and 10-nitro oleic acid or 15-deoxy-12,14-prostaglandin J2.

Example 3. Decidual Cell FKBP51-Progesterone Receptor Binding Mediates Maternal Stress-Induced Preterm Birth Preterm birth (PTB), characterized by parturition prior to 37 completed weeks of gestation, has a 5 to 18% prevalence and accounts globally for over 15 million births per year. In 2018, the PTB rate in the U.S. was 10.0% of livebirths making it the leading cause of perinatal morbidity and mortality. It is also a major cause of childhood lung disease and neurodevelopmental disabilities, contributing to $26 billion/year in health care costs. Up to 80% of PTBs occur spontaneously, whereas ~20% are indicated by deteriorating maternal or fetal conditions. While ascending genital tract infections, abruptions, and multiple gestations account for more than half of PTBs, maternal stress-associated with depression and post-traumatic stress disorder, and fetal stress-related to abnormal placentation are strongly implicated in many idiopathic PTBs (iPTBs). However, the underlying molecular mechanism(s) responsible for stress-associated PTB remain unclear.

In all viviparous species, inhibition of progesterone (P4) production and/or function elicits labor (i.e. induces decidual inflammation, remodels the cervix, promotes fetal membrane rupture and increases myometrial contractility). P4 signaling in target cells is achieved by binding to progesterone receptor (PR) isoforms which belong to a ligand-activated nuclear transcription factor superfamily Ligand binding to PR induces receptor dimerization, phosphorylation and binding to PR response elements on DNA to modulate transcription of target genes. Unlike most mammals in which parturition is initiated by declining maternal plasma P4 levels, during higher primate and guinea pig parturition, elevated P4 levels are sustained until after delivery of the placenta indicating that a physiologic block of P4 signaling in target cells elicits "functional P4 withdrawal". Treatment of women with PR antagonists (e.g. RU486) and prostanoids induces labor at any stage of pregnancy. Mechanisms contributing to functional P4 withdrawal include decreased PR levels, changes in PR co-regulators, and/or indirect antagonism by other transcription factors.

In the uterus, PR expression appears to be greatest in the decidua, which is located between the fetal membrane and myometrium. Placental, chorionic and amniotic cells fail to express demonstrable levels of PR, while expression of total PR in the myometrium is lower than in the decidua. Moreover, the decidua represents a major source of prostaglandins and proteases that are crucial to parturition. Thus, decidual cells appear to be a crucial arbiter of both term and PTB. It was shown that decidual stromal cells in both the decidua basalis and parietalis display significantly reduced nuclear PR protein expression among patients in term labor as well as those with chorioamnionitis- or abruption-associated PTB compared to non-laboring gestational age (GA)-matched controls. In support of these in situ findings, the in vitro analysis revealed that primary third trimester decidual cell cultures display reduced PGR mRNA and protein levels in response to interleukin 1β or thrombin, the major molecular mediators of chorioamnionitis and abruption, respectively. Collectively, these results indicate that decidual cells are the central target of P4 signaling and that decidual nuclear PR levels are critical in maintaining human pregnancy with a substantial decrease in PR expression inducing human parturition by causing functional P4 withdrawal.

The FK506-binding proteins, FKBP51 and 52, are immunophilins that assemble as co-chaperones with heat shock protein 90, p23, as well as steroid receptors including glucocorticoid receptor (GR) and PR. FKBP52 enhances, whereas FKBP51 attenuates PR- and GR-mediated transcription. Robust upregulation of FKBP51 levels by ligand activated GR, and to a lesser extent by ligand activated PR, is well established. It was found that: 1) in cultured primary human decidual cells, FKBP51, but not FKBP52 levels, are up-regulated by either dexamethasone, a pure glucocorticoid, or medroxyprogesterone acetate, a mixed progestin-glucocorticoid, whereas Organon 2058, a pure progestin agonist exerted minimal stimulatory effects; 2) overexpression of FKBP5 resulted in inhibition of PR binding to PRE; and 3) at the maternal-fetal interface, FKBP51 is predominantly expressed in decidual cell nuclei with increased expression in term decidual cells among patients in labor compared with non-laboring controls. Taken together, these findings provide an additional mechanism of functional P4 withdrawal via FKBP51-mediated inhibition of PR transcriptional activity.

As a stress-responsive protein, FKBP51 gene polymorphisms are associated with increased FKBP51 expression levels and are linked to depression and stress-related disorders, known risk factors for PTBs. Depletion of Fkbp5 in mice protects against stress-induced hormonal changes as well as depressive and anxiety-like behaviors, indicating FKBP51 as a promising new target for stress-related disorders. Therefore, induced increased FKBP51 expression can promote functional P4 withdrawal by inhibiting PR transcriptional activity to cause PTB. Conversely, depletion of Fkbp5 prevents PTB in response to maternal stress. Experiments were performed to test: 1) FKBP51 and PR levels were measured in decidual specimens collected from women with iPTB and in GA-matched controls; 2) the physical interaction between FKBP51 and PR was assessed in these samples; and 3) the effect of Fkbp5 deletion was evaluated in a murine model of stress-induced PTB.

Figures 6A, 6B, 6C, 6D, 6E, 6F:
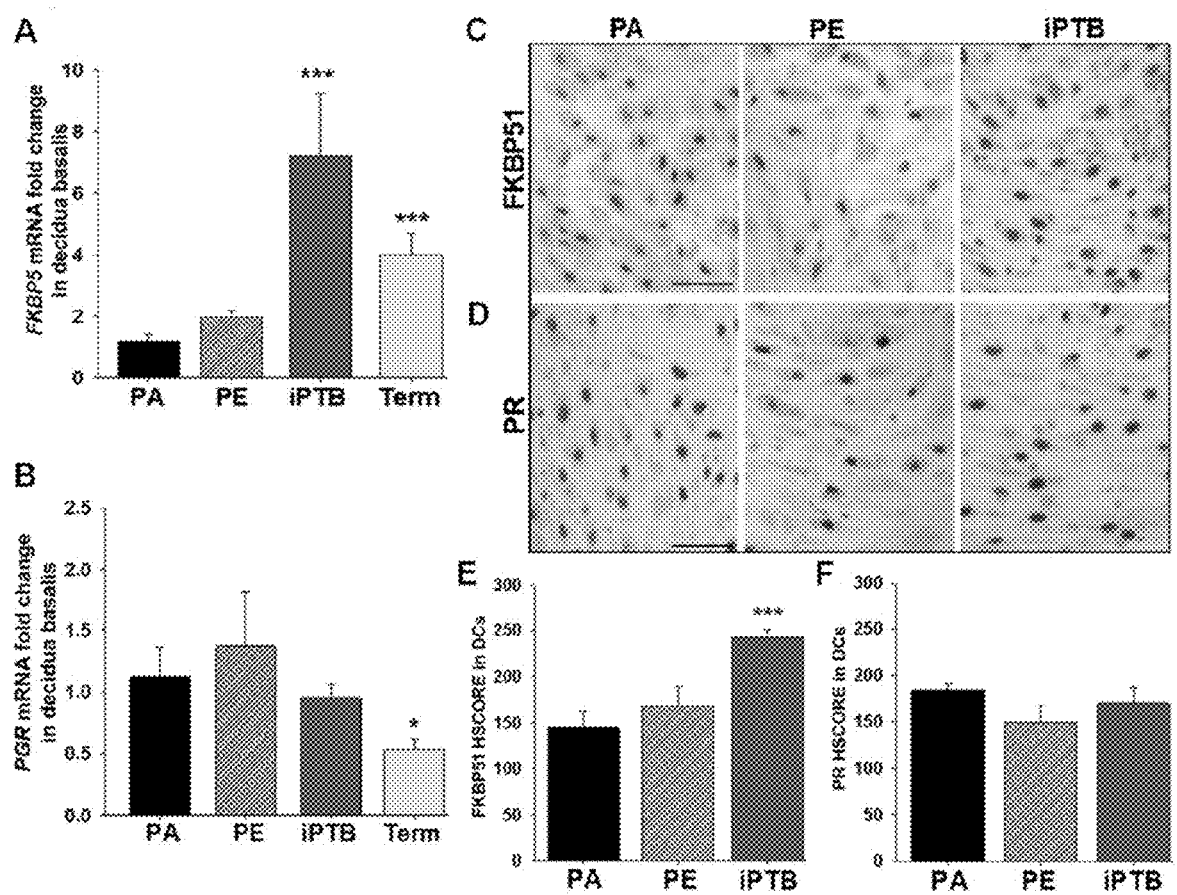
FIGS. 6A-6F show decidual cells at the maternal-fetal interface from a placenta obtained following idiopathic PTB displaying enhanced FKBP5 mRNA and protein levels.
Figure 13:
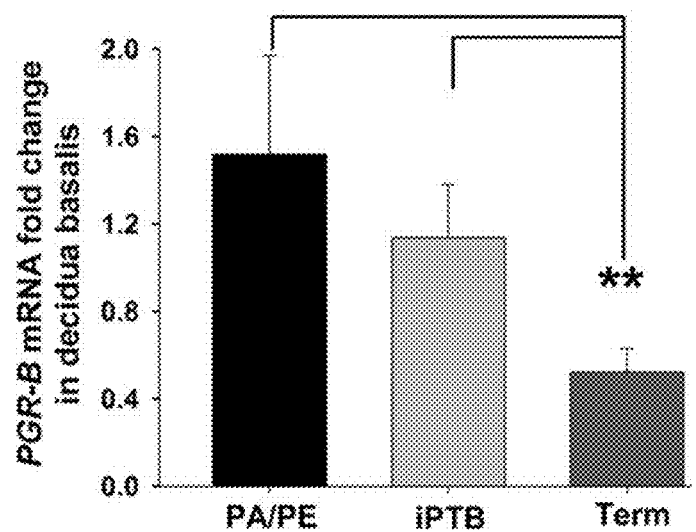
FIG. 13 shows progesterone receptor-B (PGR-B) expression levels in human decidual cells. PGR-B mRNA expression levels in decidua basalis from placenta collected from placenta accrete and preeclampsia (PA/PE, n=14), idiopathic preterm birth (iPTB, n=9) and term specimens (n=10) by qPCR. Data represent mean±SEM; **P<0.01 vs. PA/PE specimens by One Way ANOVA with Dunn's method.

Enhanced Decidual Expression of FKBP51 mRNA and Protein in iPTB. It was previously shown that decreased PR and increased FKBP51 expression in the nuclei of decidual cells in placental sections obtained from laboring vs. non-laboring women at term, indicating a contributing role for FKBP51 in mediating decidua specific functional P4 withdrawal during parturition. To investigate if these molecular changes also occur in decidua obtained from iPTB specimens, FKBP5 and PGR expression was assessed by qPCR in decidua basalis specimens obtained from women with iPTB compared with two control groups: 1) negative control—GA-matched women with elective PTB for placenta accreta (PA) or indicated PTB for preeclampsia (PE); or 2) positive control—women in labor at term. Decidual FKBP5 mRNA levels were similarly elevated in both term labor (Mean±SEM: 4.01±0.68) and iPTB (7.22±2.01) specimens, and both were significantly higher than FKBP5 mRNA levels found in PA (1.18±0.22) or PE samples (1.98±0.21; FIG. 6A). PGR mRNA levels were similarly decreased in term labor (0.50±0.07) and iPTB (0.83±0.11) specimens and PGR mRNA expression term labor specimens were significantly lower compared with PA (1.12±0.24) or PE (1.37±0.44) specimens (FIG. 6B), whereas PGR mRNA levels in iPTB specimens (0.83±0.11) trended lower without attaining statistical significance (FIG. 6B). The primers used to detect PGR mRNA levels recognized both PGR isoforms A and B, therefore, we performed another qPCR using the primer set that recognized only PGR-B levels, and the same pattern of mRNA expression was observed that compared with GA-control (PA/PE) specimens, PGR-B mRNA levels were significantly lower in term, but not in iPTB specimens (FIG. 13), indicating that PR isotype switching does not occur in decidual cells with labor.

To confirm that changes in FKBP5 and PGR mRNA levels reflect parallel changes in protein expression, sections obtained from GA-matched patients with PA- or PE-associated PTBs and iPTBs were evaluated for FKBP51 and PR protein levels by immunohistochemistry. Double immunostaining for vimentin, to identify decidual cells, and either anti-FKBP51 or anti-PR antibodies was performed. HSCORE analysis detected significantly higher FKBP51 immunoreactivity in decidual cells from iPTB (242.92±7.30) vs. both PA (144.64±18.29) or PE (168.16±20.82) specimens (FIGS. 6C and 6E). Consistent with the mRNA findings, reductions in PR immunoreactivity in iPTB vs. PA or PE specimens did not attain statistical significance (FIGS. 6D and 6F).

Figures 7A, 7B:
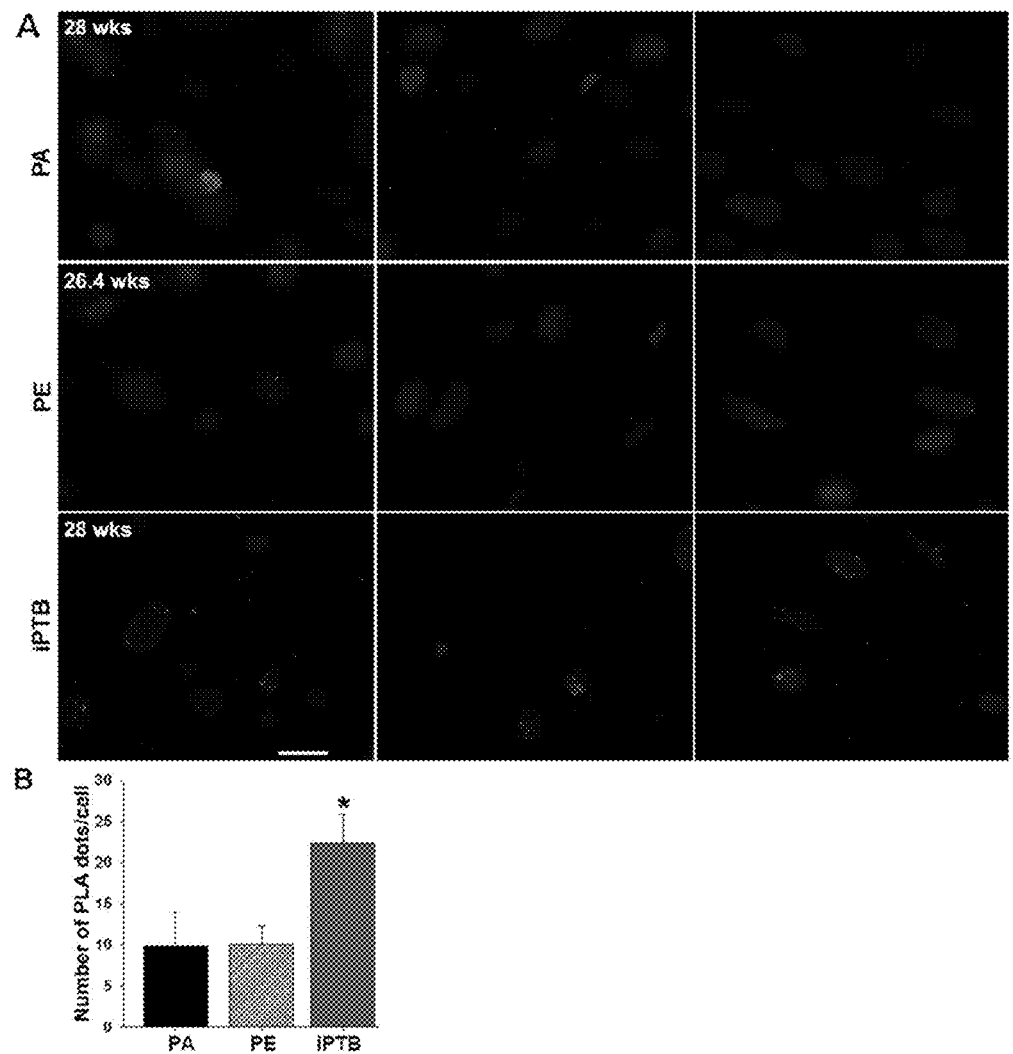
FIGS. 7A-7B show increased FKBP51 and PR interactions in nuclei of decidual cells in idiopathic preterm birth (iPTB) specimens.
Figures 14A, 14B, 14C:
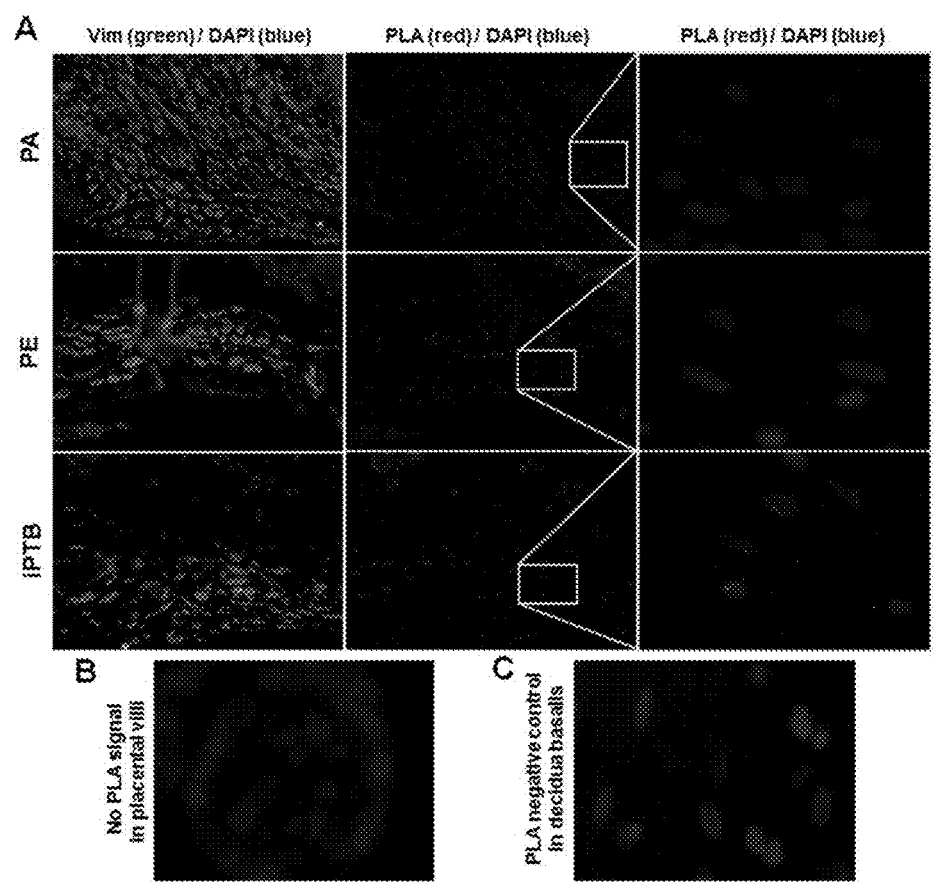
FIGS. 14A-14C show specificity of in situ proximity ligation assay for the interaction between FKBP51 and PR proteins in decidual cells.

Increased Decidual Cell Nuclear FKBP51-PR Binding in iPTB Specimens. To detect direct interaction between FKBP51 and PR proteins, in situ proximity ligation assays (PLA) was performed in decidua basalis specimens from women with iPTB vs. GA-matched women with PA or PE-associated PTBs. Again, vimentin immunofluorescence staining was used to identify decidual cells in serial sections. PLA-positive signaling was observed, indicating an interaction between FKBP51 and PR, primarily located in the nucleus of decidual (vimentin positive) cells (FIG. 7A and FIG. 14A), but not in trophoblasts (FIG. 14B). No signal was detected in decidual cells used as a negative control by withholding primary antibodies (FIG. 14C). Computer-based quantification of PLA positive signals revealed that the number of PLA signals was significantly higher in iPTB (22.42±3.46) vs. GA-matched PE (10.07±2.15) or PA specimens (9.85±4.11; FIGS. 7A-7B).

Figures 8A, 8B, 8C, 8D:
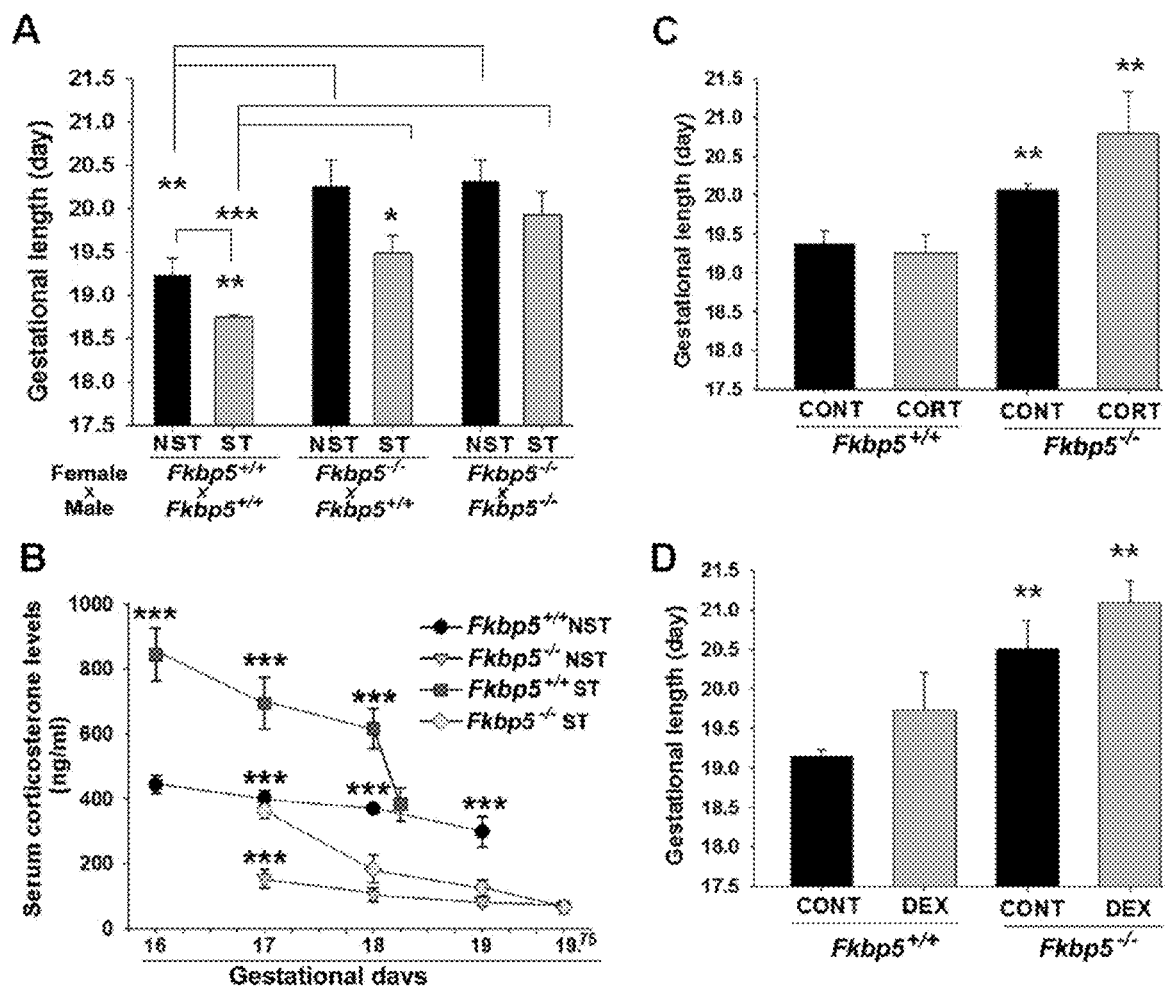
FIGS. 8A-8B show that prolonged gestation and resistance to maternal stress induced PTB in Fkbp5$^{-/-}$ mice.
FIGS. 8C and 8D show gestational length in corticosterone (CORT, n=6.
Figures 15A, 15B:
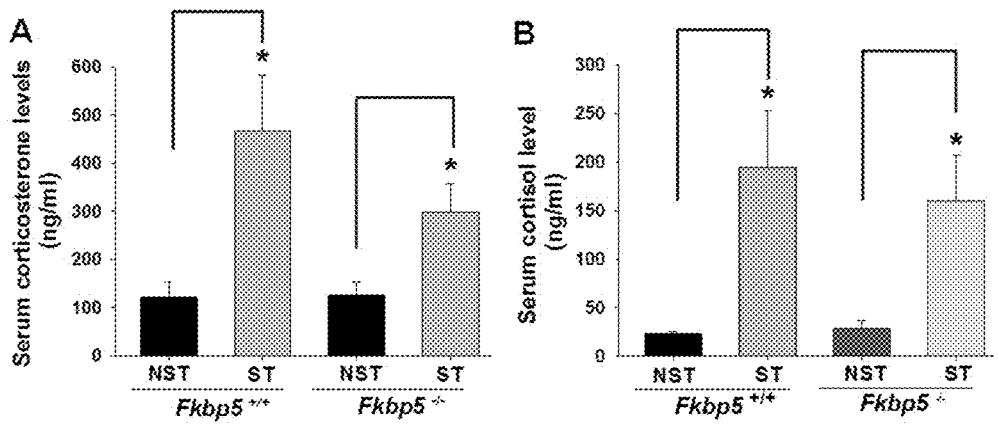
FIGS. 15A-15B show that maternal stress elevates murine corticosterone and cortisol levels. Serum corticosterone (FIG. 15A) and cortisol (FIG. 15B) levels at gestational day 11 obtained from Fkbp5$^{+/+}$ and Fkbp5$^{-/-}$ mice under non-stress (NST) or stress (ST) conditions. Data represent mean±SEM; n=5/each. *P<0.05 vs. NST-Fkbp5$^{+/+}$ or NST-Fkbp5$^{-/-}$ by One Way ANOVA with Student-Newman-Keuls test.

Fkbp5 Deficiency Prolongs Normal Gestation and Counteracts Maternal-Stress Induced PTB. To assess the role of Fkbp5 in the onset of parturition at term as well as stress-induced PTB, Fkbp5 knockout (Fkbp5$^{-/-}$) and wild type (Fkbp5$^{+/+}$) mice were employed subjected to either a physiologic unrestrained normal state (NST) or maternal restraint-induced stress (ST). First, Fkbp5$^{+/+}$ and Fkbp5$^{-/-}$ female mice were mated with adult Fkbp5$^{+/+}$ male mice to examine the relative contribution of maternal genotype to gestational length under unrestrained or restrained conditions. Restraints were applied three times/day for 60 min starting at embryonic day 8 (E8) through E18. Plasma corticosterone and cortisol were measured as biomarkers of chronic and acute stress, respectively, at E11. As anticipated, maternal stress increased serum corticosterone and cortisol levels by 3.8- and 8.4-fold, respectively, in Fkbp5$^{+/+}$ mice, and 2.3- and 5.7-fold, respectively, in Fkbp5$^{-/-}$ mice (FIGS. 15A and 15B). In unrestrained mice, gestational length was significantly prolonged in Fkbp5$^{-/-}$ (20.25±0.29 days) vs. Fkbp5$^{+/+}$ mice (19.22±0.19 days; FIG. 8A). While maternal stress significantly reduced gestational length in Fkbp5$\pm^{1}\pm$ (18.74±0.03) as well as in Fkbp5$^{-/-}$ (19.48±0.19) mice, stress-associated gestational length was significantly longer in Fkbp5$^{-/-}$ vs. Fkbp5$^{+/+}$ mice (FIG. 8A).

To examine the net contribution of both maternal and fetal Fkbp5$^{-/-}$ genotype to gestational length, Fkbp5$^{-/-}$ female mice were also mated with adult Fkbp5$^{-/-}$ male mice and pregnant mice were maintained under unrestrained and restrained conditions. In the absence of stress, Fkbp5$^{-/-}$ female mice mated with Fkbp5$^{-/-}$ males did not display longer gestations compared with in Fkbp5$^{-/-}$ females mated with Fkbp5$^{+/+}$ males (20.31±0.24 vs. 20.25±0.29 days). However, restrained Fkbp5$^{-/-}$ mice mated with Fkbp5$^{-/-}$ males (19.93±0.25) displayed longer gestations compared to restrained Fkbp5$^{-/-}$ females mated with Fkbp5$^{+/+}$ males. Moreover, there was no significant difference in gestational length among unrestrained vs. restrained Fkbp5$^{-/-}$ mice mated with Fkbp5$^{-/-}$ males (P=0.18; FIG. 8A). Collectively, these results indicate that: 1) Fkbp5$^{-/-}$ mice have longer gestation than Fkbp5$^{+/+}$ mice; 2) maternal restraint stress induces PTB; and 3) Fkbp5$^{-/-}$ female mice mated with Fkbp5$^{-/-}$ males display maximal resistance to stress-induced PTB. While restraint stress elevated glucocorticoid levels (FIG. 8B) and shorten gestation in wild type females and Fkbp5$^{-/-}$ females mated with Fkbp5$^{+/+}$ males (FIG. 8A), pharmacological doses of both corticosterone (CORT) and dexamethasone (DEX) did not shorten gestation in any of these mouse genotypes (FIGS. 8C-8D).

Figures 16A, 16B, 16C, 16D:
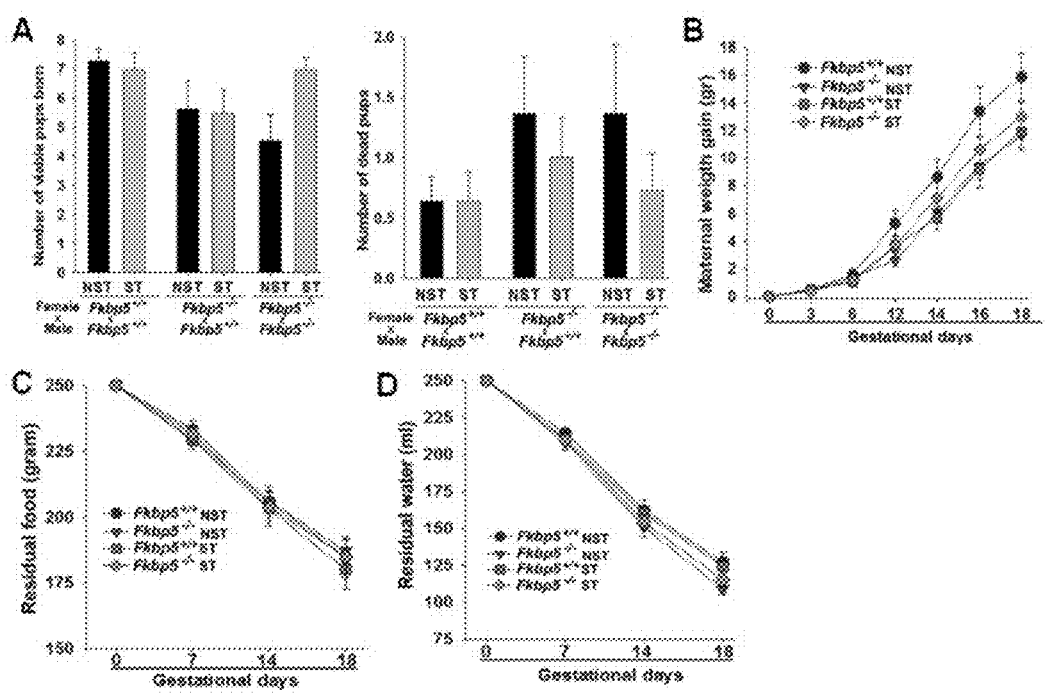
FIGS. 16A-16D. Neither maternal stress nor Fkbp5 deficiency affect litter size, maternal weight gain, food, and water intake during pregnancy.

Whether either maternal stress or Fkbp5$^{-/-}$ deficiency affected litter size or gender ratio was also evaluated and it was found that pup numbers at parturition (FIG. 16A) as well as the sex ratio of the pups did not differ among genotypes. The number of stillbirths also did not differ among groups (FIG. 16A). Previous studies demonstrated that Fkbp5$^{-/-}$ mice have reduced bodyweights compared to wild-type littermates and that they are resistant to diet-induced obesity. Therefore, maternal weight gains as well as food and water intake during pregnancy was measured under normal or stress conditions. Maternal weight gain did not differ among groups between E0 through E18 (FIG. 16B). Moreover, no significant difference was observed in food consumption and water intake throughout gestation among the groups (FIGS. 16C-16D).

Maternal Stress-Induced PTB Is Not Associated with Systemic P4 Withdrawal.

Figures 9A, 9B, 9C:
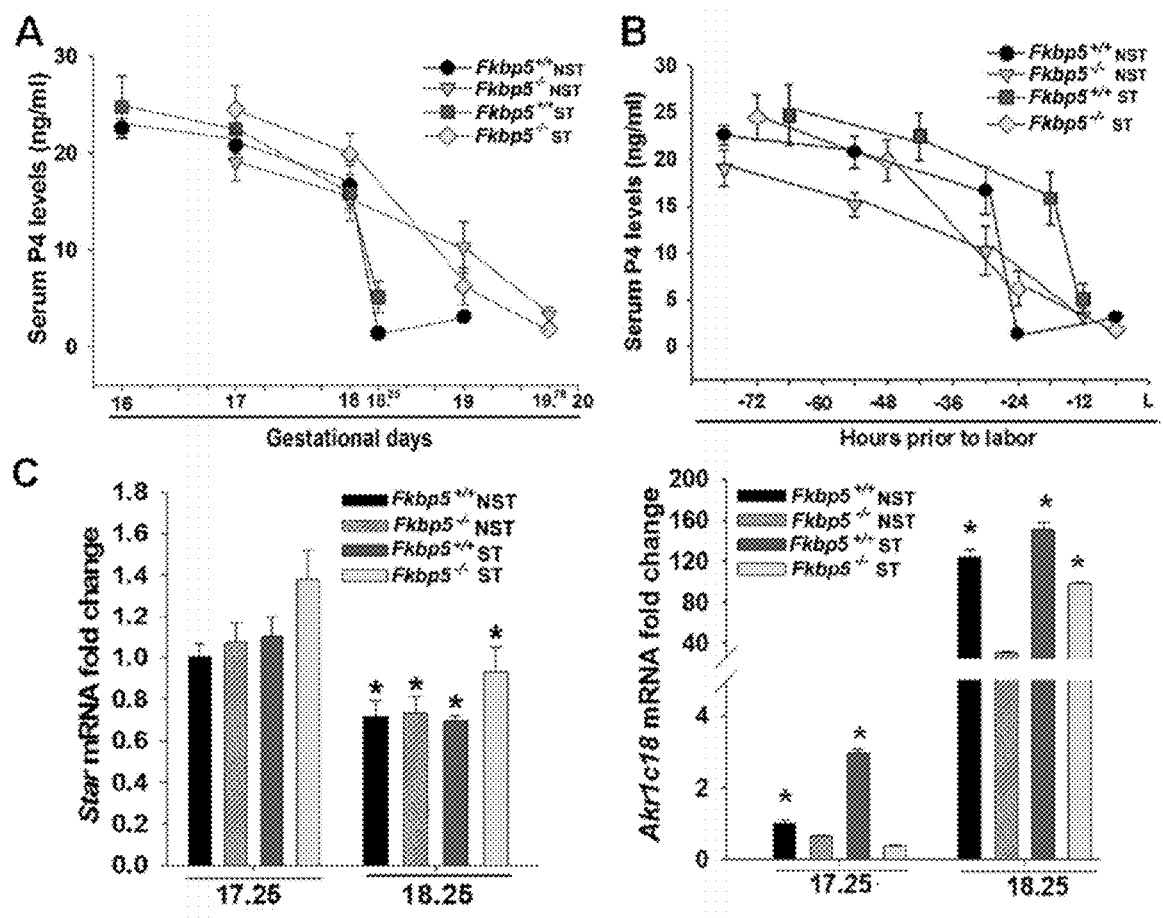
FIGS. 9A-9C show that progesterone withdrawal is not impaired in Fkbp5$^{-/-}$ mice.

Luteal regression precedes labor in mice accompanied by a reduction in serum P4 levels. Thus, serum P4 levels were measured in the final 72 hours of gestation in all groups by ELISA. Both unrestrained and restrained $Fkbp5^{+/+}$ mice displayed similar serum P4 levels between E16-E18, with a dramatic decrease on E18.25 (FIG. 9A). The decline in serum P4 levels in $Fkbp5^{-/-}$ mice was similar to $Fkbp5^{+/+}$ mice on E17 and E18, but not as great as in unrestrained $Fkbp5^{+/+}$ mice on E19. The increased rate of decline of serum P4 levels were not different between either restrained $Fkbp5^{+/+}$ vs. unrestrained $Fkbp5^{+/+}$ or restrained $Fkbp5^{-/-}$ vs. unrestrained $Fkbp5^{-/-}$ (FIG. 9A). Thus, systemic P4 withdrawal does not mediate maternal restraint induced PTB. Further analysis of serum P4 levels according to time to delivery also supported the lack of an association between systemic P4 decline and maternal-stress induced PTB (FIG. 9B).

Figures 17A, 17B:
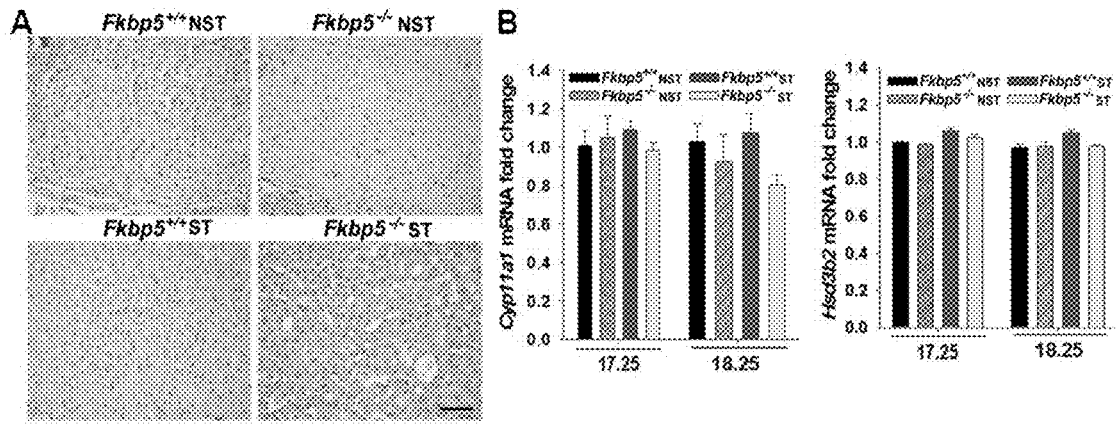
FIGS. 17A-17B show that Fkbp5 deletion does not affect corpus luteal structure.
Figures 18A, 18B, 18C:
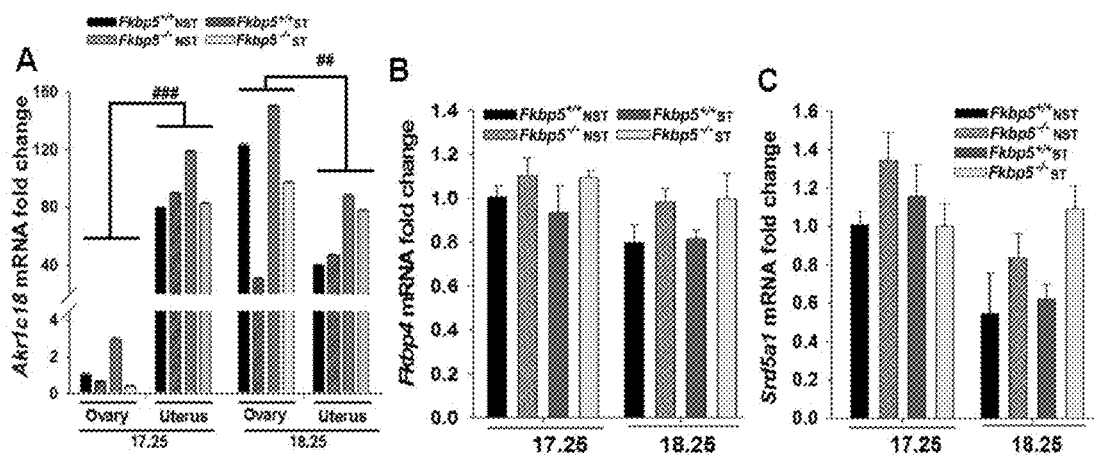
FIGS. 18A-18C show expression of Akr1c18, Fkbp4 and Srd5a1.

Ovarian luteal histology was evaluated by H&E staining and the size and appearance of the corpus lutea were comparable among groups at E18.25 (FIG. 17A). We also evaluated ovarian expression levels of enzymes involved in either P4 synthesis or metabolism, including steroidogenic acute regulatory protein (Star), cytochrome P450 family 11 subfamily a member 1 (Cyp11a1), and hydroxy-delta-5-steroid dehydrogenase, 3 beta- and steroid delta-isomerase 2 (Hsd3b2), to represent key P4 synthetic enzymes as well as aldo-keto reductase family 1, member C18 (Akr1c18; aka 20α-hydroxysteroid dehydrogenase; 20α-HSD), an enzyme that inactivates P4 by converting it to 20-α-dihydroprogesterone. Comparisons by qPCR analysis revealed similar ovarian expression levels of Cyp11a1 and Hsd3b2 mRNA among all groups at either E17.25 or E18.25 (FIG. 17B), whereas a significant decrease in Star expression occurred in all groups at E18.25 vs. E17.25 (FIG. 9C). Interestingly, the ovaries of unrestrained or restrained $Fkbp5^{-/-}$ mice displayed lower Akr1c18 expression levels than either unrestrained or restrained $Fkbp5^{+/+}$ mice at both E17.25 and E18.25. However, Akr1c18 levels were not significantly different between unrestrained and restrained $Fkbp5^{+/+}$ mice at E18.25 (FIG. 9C). Remarkably, comparison of ovarian and uterine expression of Akr1c18 mRNA levels in unrestrained $Fkbp5^{+/+}$ mice revealed 79.6-fold higher Akr1c18 levels in the uterus at E17.25 (FIG. 18A). A similar pattern was also observed for restrained $Fkbp5^{+/+}$ or unrestrained $Fkbp5^{-}$ or restrained $Fkbp5^{-/-}$ mice at E17.25 (FIG. 18A), indicating that local P4 metabolism is predominately initiated in the uterus at E17.25 and occurs subsequently in the ovary at E18.25.

Figures 10A, 10B, 10C, 10D:
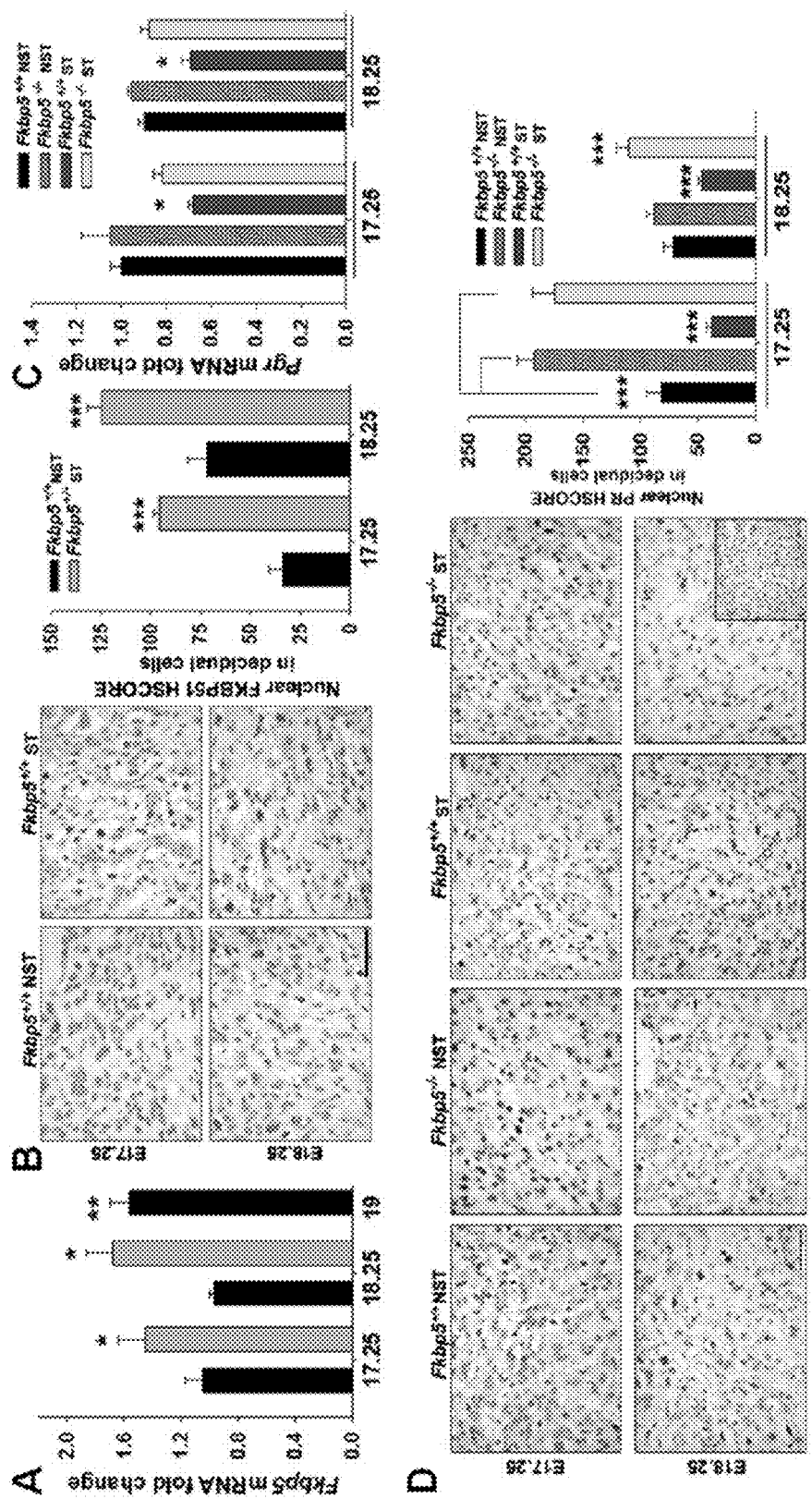
FIGS. 10A-10D show increased FKBP51 and reduced progesterone receptor expression in maternal-stress induced Fkbp5$^{+/+}$ mice.

Maternal Stress Induced FKBP51 and Reduced Uterine PR Expression. A similar pattern of decline in serum P4 levels between restrained and unrestrained mice coupled with the predominant Akr1c18 mRNA expression in uterine tissues indicates that functional P4 withdrawal and/or increased local P4 metabolism in uterine tissues contribute(s) to maternal-stress induced PTB. Uterine expression of Fkbp5 and Fkbp4, Pgr and P4 metabolizing enzymes Akr1c18 and Srd5a1 (5α-reductase was measured, which metabolizes P4 to 5α-pregnane-3,20-dione and is primarily expressed in uterus). Consistent with the findings in human decidua (FIGS. 6A-6F), uteri of unrestrained $Fkbp5^{+/+}$ mice displayed a significant increase in Fkbp5 levels at E19 vs. E17.25 or E18.25 (FIG. 10A), and maternal stress significantly elevated Fkbp5 levels in $Fkbp5\pm^{1}\pm$mice at both E17.25 and E18.25 compared with unrestrained $Fkbp5^{+/+}$ mice (FIG. 10A). In contrast to these findings for Fkbp5 expression, levels of Fkbp4, which encodes FKBP52 protein, revealed no significant changes among the groups (FIG. 18B), indicating no contribution of FKBP52 levels to maternal-stress induced PTB Immunohistochemical analysis of uterine sections confirmed increased FKBP51 protein levels in restrained vs. unrestrained $Fkbp5^{+/+}$ mice (FIG. 10B). Maternal stress also significantly down-regulated Pgr mRNA levels in uterine tissues of $Fkbp5^{+/+}$ mice, but not in $Fkbp5^{-/-}$ mice on both E17.25 and E18.25 (FIG. 10C). HSCORE analysis of immunostained uterine sections confirmed significantly lower PR protein levels in decidual cell nuclei in restrained $Fkbp5^{+/+}$ mice vs. all other groups at both E17.25 and E18.25 (FIG. 10D).

Figures 11A, 11B:
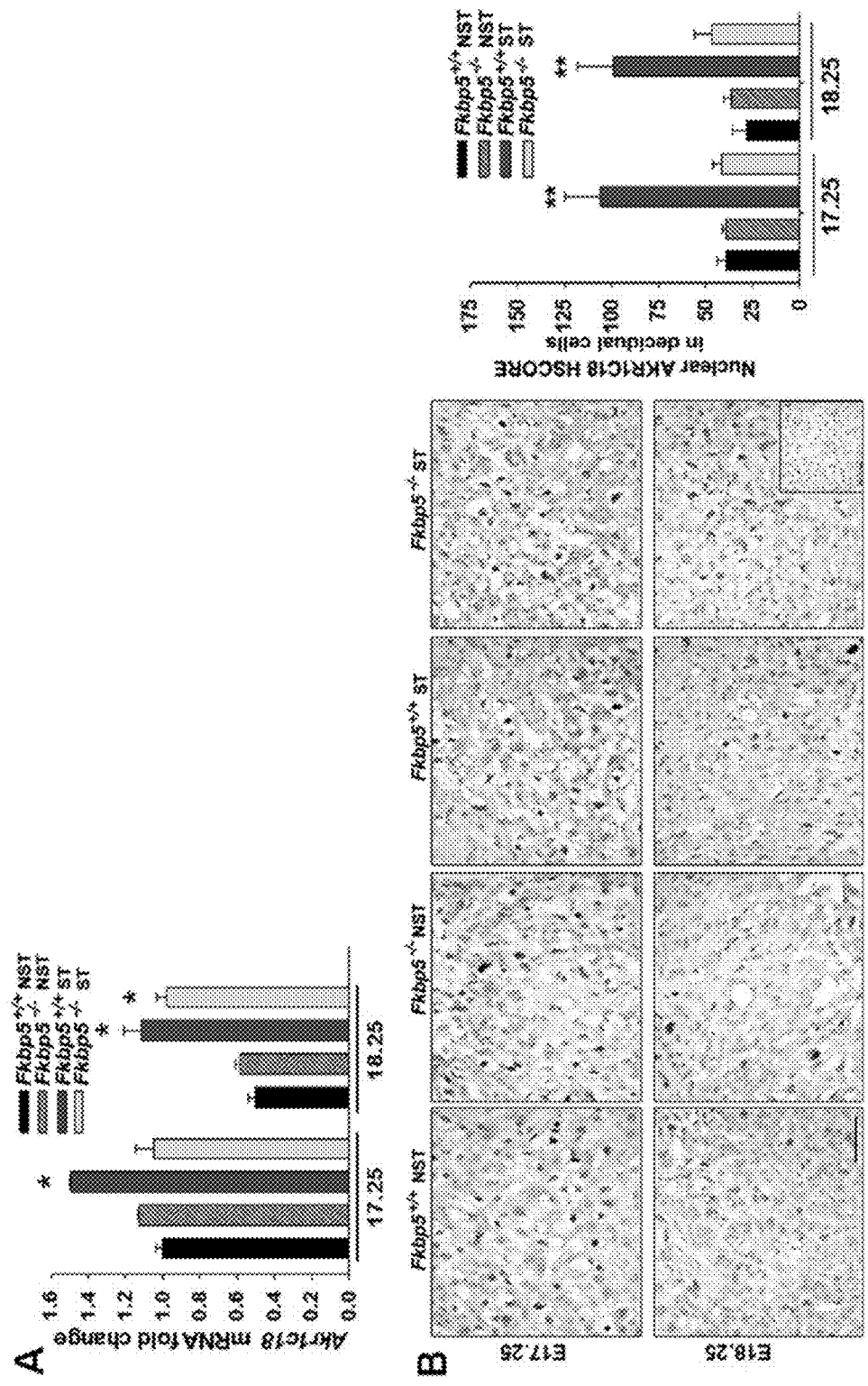
FIGS. 11A-11B show increased AKR1C18 expression in maternal-stress induced Fkbp5$^{+/+}$ mice.
Figures 12A, 12B, 12C, 12D:
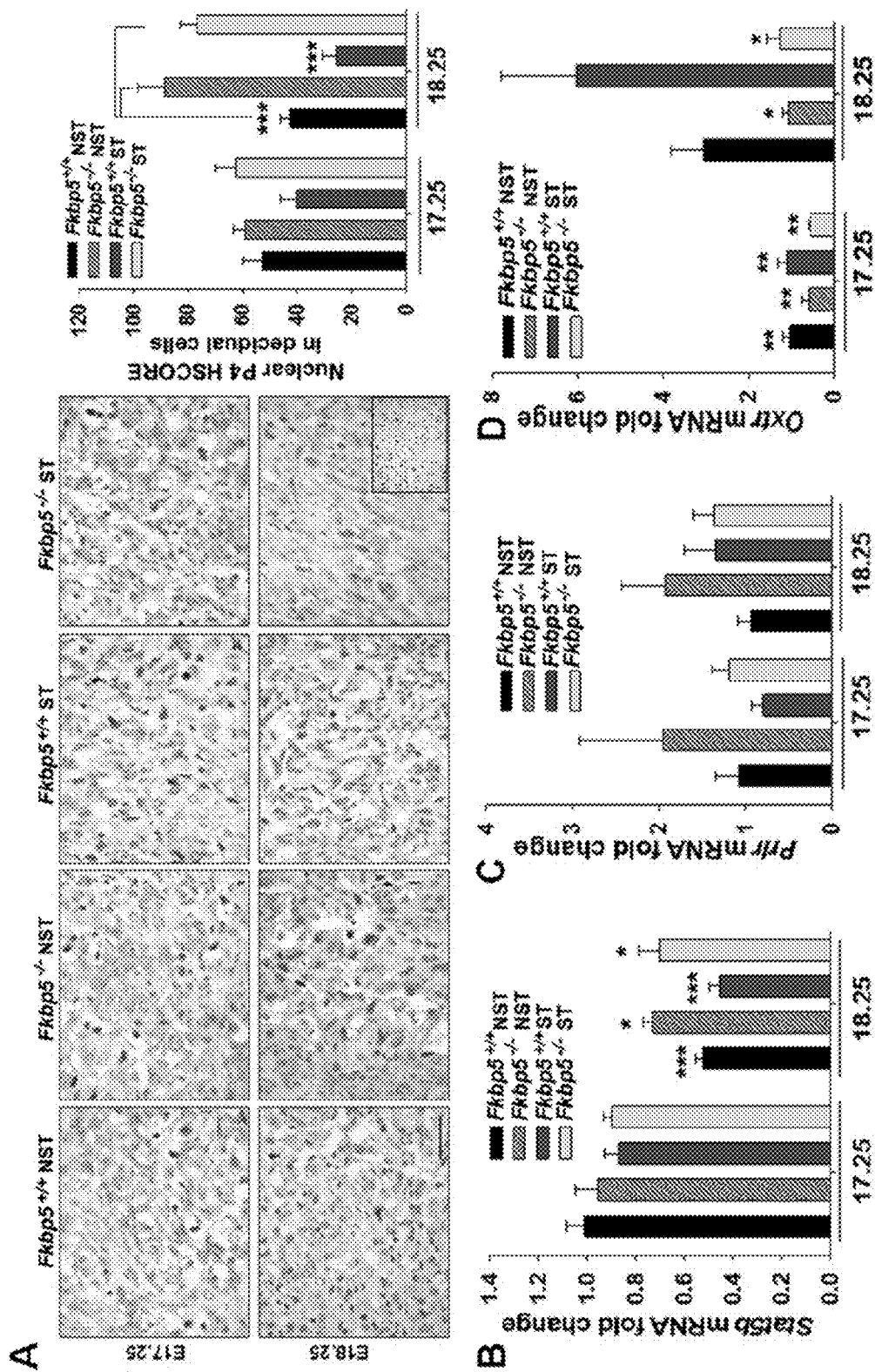
FIGS. 12A-12D show reduced progesterone (P4) and Stat5b levels and increased Oxtr levels in the uteri of Fkbp5$^{+/+}$ mice.
Figure 19:
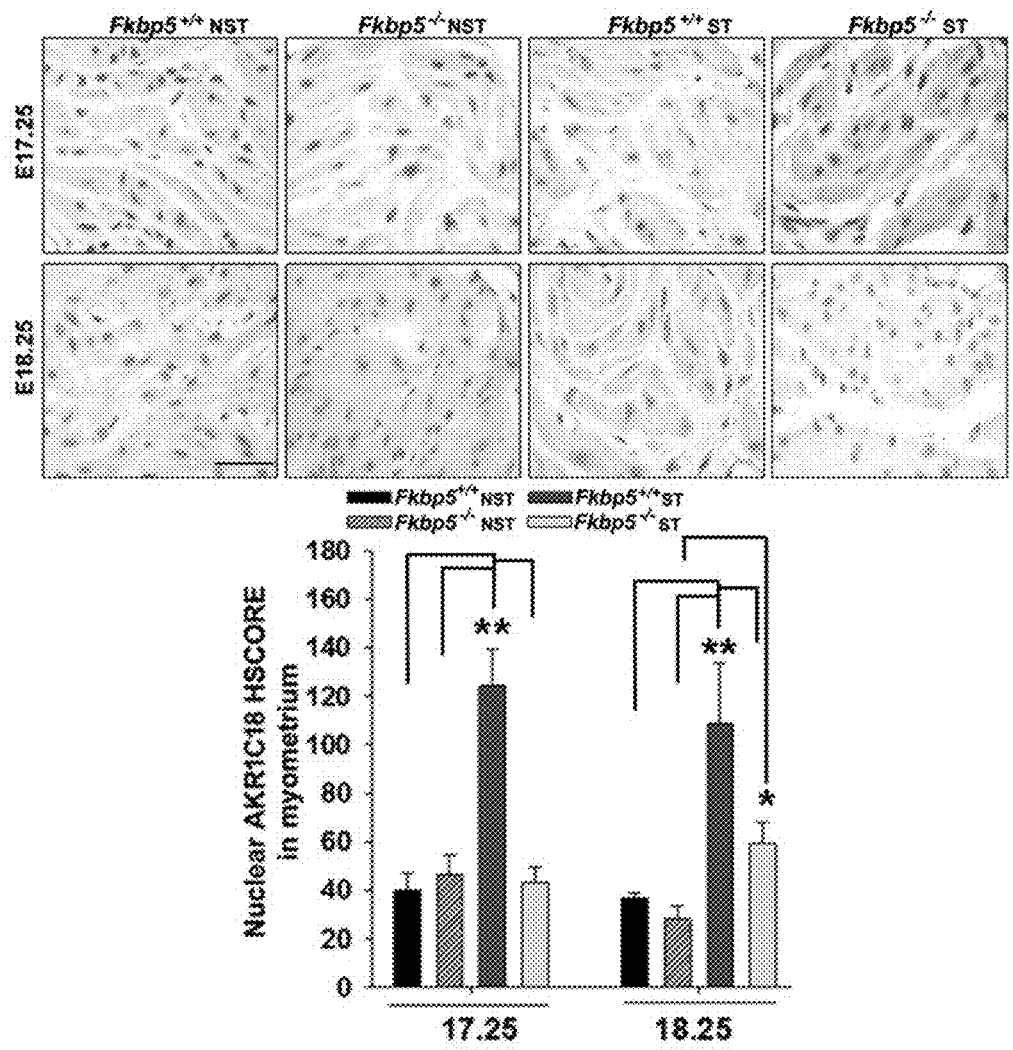
FIG. 19 shows increased AKR1C18 levels in maternal stress-induced Fkbp5$^{+/+}$ mice. Myometrial AKR1C18 immunoreactivity in uterine tissues from Fkbp5$^{+/+}$ and Fkbp5$^{-/-}$ mice under non-stress (NST) or stress (ST) conditions at E17.25 and E18.25. Bars represent mean±SEM myometrial nuclear AKR1C18 HSCOREs (n=7/each). Scale: 20 µm. Inset micrograph shows negative control staining; **P<0.01 and *P<0.05 by One Way ANOVA with Student-Newman-Keuls test.

To evaluate the contribution of local uterine P4 metabolism to maternal stress-induced PTB, expression levels of Akr1c18 and Srd5a1 was assessed. Deficiency of either gene has been shown to prolong gestation independent of systemic P4 levels in mice. Uterine Srd5a1 expression was similar among all groups on either E17.25 or E18.25 (FIG. 18C). In contrast, uterine Akr1c18 levels were significantly upregulated in the uteri of restrained $Fkbp5^{+/+}$ mice compared to the other three groups at E17.25. At E18.25, uterine Akr1c18 expression levels are similar in restrained $Fkbp5^{+/+}$ and restrained $Fkbp5^{-/-}$ mice, and significantly higher than in unrestrained $Fkbp5^{+/+}$ and $Fkbp5^{-/-}$ mice (FIG. 11A) Immunohistochemical staining displays both nuclear and cytoplasmic localization of AKR1C18 protein in decidual cells in mice. HSCORE analysis of immunostained uterine sections confirmed significantly elevated AKR1C18 protein levels in the nuclei of decidual (FIG. 11B) and myometrial (FIG. 19) cells of restrained $Fkbp5^{+/+}$ mice vs. all other groups at both E17.25 and E18.25. To confirm that elevated AKR1C18 expression correlates with local reduction in P4 levels, HSCORE analysis was performed in uterine sections immunostained for P4. At E17.25, nuclear P4 levels are similar among all groups in decidua, but significantly lower at E18.25 in unrestrained $Fkbp5^{+/+}$ and restrained $Fkbp5^{+/+}$ vs. unrestrained $Fkbp5^{-/-}$ or restrained $Fkbp5^{-/-}$ mice (FIG. 12A), and among wild type mice there was a significant reduction observed in decidua of restrained $Fkbp5^{+/+}$ vs. unrestrained $Fkbp5\pm^{1}\pm$mice. However, restraint had no effect on nuclear P4 staining in either restrained or unrestrained $Fkbp5^{-/-}$ mice (FIG. 12A).

Signal transducer and activator of transcription 5b (Stat5b) deficiency shortens gestational length in mice by prematurely inducing AKR1C18 levels. Prolactin binding to its receptor in decidual cells activates STAT5B signaling to inhibit AKR1C18 expression preventing P4 metabolism, thereby contributing to the physiologic maintenance of pregnancy. Thus, uterine Stat5b (FIG. 12B) and prolactin receptor (Prlr) expression (FIG. 12C) were evaluated, and it was found that Stat5b levels are significantly lower in unrestrained $Fkbp5^{+/+}$ and restrained $Fkbp5^{+/+}$ vs. unrestrained $Fkbp5^{-/-}$ or restrained $Fkbp5^{-/-}$ mice at E18.25 (FIG. 12B), whereas Prlr mRNA levels did not change among the groups at either E17.25 or 18.25 (FIG. 12C). Finally, evaluation of expression of oxytocin receptor (Oxtr), which induces myometrial contraction, revealed significantly higher levels in unrestrained $Fkbp5^{+/+}$ and restrained $Fkbp5^{+/+}$ vs. unrestrained $Fkbp5^{-/-}$ or restrained $Fkbp5^{-/-}$ mice at E18.25, with a significant increase in all groups at E18.25 vs. E17.25 (FIG. 12D).

Despite the initial promise that P4 therapy decreased recurrence risk of PTB as well as the risk of PTB among patients with a short cervix, recent large randomized trials have not confirmed its efficacy. The failure of such therapy, coupled with observations that PR antagonist therapy±prostaglandins induce labor at all gestational ages indicates that functional P4 withdrawal mediated at the level of the PR triggers human labor. This is further supported by previous findings that term labor is associated with reduced decidual PR and increased decidual FKBP51 expression and that chorioamnionitis and abruption, major etiologies of early PTB, are associated with reduced PR expression. Demonstrated herein is that idiopathic and stress associated PTB, major causes of late PTB, are also triggered by functional P4 withdrawal, albeit mediated through increased FKBP51 expression.

Prior studies demonstrated that glucocorticoid exposure significantly up-regulates decidual cell FKBP51 mRNA and protein expression. Moreover, overexpression of FKBP5 inhibits PR binding to its canonical DNA response element in decidual cells, while PR binding to PRE is increased in decidual cells in which FKBP5 has been silenced. Taken together, these findings indicate that rising fetal, placental and/or maternal glucocorticoid levels prior to both term and iPTB trigger functional P4 withdrawal resulting from increased decidual cell FKBP51 expression. Significantly enhanced FKBP51-PR interaction in human decidual cell nuclei of iPTB specimens as revealed by PLA analysis in the current study provides further evidence for this pathway of functional P4 withdrawal causing iPTB.

An Fkbp5 knockout mouse was employed to define the in vivo function of FKBP51 on gestational length as well as its role in maternal stress induced PTB. This is the first study demonstrating prolonged gestation in Fkbp5$^{-/-}$ mice, indicating that FKBP51 plays a crucial role on gestational length and/or initiation of parturition. Both maternal and embryonic Fkbp5 gene expression contribute to stress-associated reductions in gestational length since the combination of maternal and embryonic Fkbp5 deficiency prolongs gestation compared to maternal deficiency alone in restrained mice. Compared to Fkbp5$^{+/+}$ mice, lower levels of ovarian and uterine Akr1c18 (20α-HSD) at E17.25 through E19 in Fkbp5$^{-/-}$ mice correlate with the delayed decline in serum P4 observed in these knockout mice and help account for their prolonged gestation. Furthermore, these results revealing higher Pgr mRNA and protein levels at E17.25 and lower Oxtr levels at E18.25 in uteri of Fkbp5$^{-/-}$ mice represent additional factors contributing to their prolonged gestation. Thus, a combination of prolonged ovarian P4 production, reduced local uterine P4 metabolism and sustained PR activity can explain the prolongation of gestation in Fkbp5$^{-/-}$ mice.

Progesterone-induced decidualization is a potent inducer of prolactin levels. Previous studies demonstrated that prolactin inhibits 20α-HSD expression by activating STAT5B signaling in both mice and rats and that Stat5b deficient mice cannot maintain pregnancy beyond E12 as a result of a dramatic decline in serum P4 levels. These results showing higher uterine Stat5b levels in Fkbp5$^{-/-}$ vs. Fkbp5$^{+/+}$ mice at E18.25, is consistent with Fkbp5 deletion preventing premature inhibition of P4 signaling and maintenance of prolactin stimulated STAT5B expression, helping to account for the pregnancy prolonging effects of Fkbp5 deletion.

Previously, two groups reported that mice with Akr1c18 (20α-HSD) deficiency also display prolonged gestation. Moreover, administration of RU486, a PR inhibitor, to Akr1c18 deficient mice at E19 resulted in normal parturition on the following day, although sufficient serum P4 levels were detected to sustain pregnancy. These findings indicate that, as occurs in humans, functional P4 withdrawal mediated by PR inhibition can also trigger parturition in mice. Thus, our finding of 80-fold greater expression of Akr1c18 in the uterus vs. ovary at E17.25, coupled with increased uterine FKBP51 levels and decreased PR levels at E18.25 in wild type mice suggest that local uterine P4 metabolism coupled with reduced PR activity rather than luteolysis initiates normal parturition in mice. Indeed, luteolysis is a consequence rather than a cause of labor in mice, reflecting increasing uterine prostaglandin production. Thus, murine parturition is analogous to human parturition since both species display decreased PR and increased FKBP51 expression in decidual cells. Moreover, consistent with the present findings in the mouse, two groups have shown increased myometrial 20α-HSD levels in term and preterm human parturition.

Stressful circumstances directly stimulate the hypothalamus-pituitary-adrenal axis to promote glucocorticoid release. Glucocorticoids then bind to their receptor to initiate GR-mediated transcriptional induction of several genes, including upregulation of FKBP5 expression. Increased FKBP51 levels, in turn, lead to FKBP51 binding to GR, which generates an intracellular negative feedback loop to inhibit GR-mediated transcription, preventing excessive and persistent stress-induced GR responses. Several studies reported strong evidence correlating FKBP5 gene polymorphisms and/or increased FKBP51 expression with enhanced susceptibility to various psychiatric diseases including post-traumatic stress disorder, major depressive disorder, and anxiety, all of which have been associated with PTB in humans. The current study demonstrates that maternal physiologic stress caused by immobilization of timed pregnant wild type mice, increases uterine Fkbp5 mRNA and protein expression at E17.25 and E18.25 and causes PTB. Moreover, combined maternal and fetal deficiency of the Fkbp5 gene prevents such stress mediated PTB. Consistent with our findings, Govindaraj et al. also showed that late restraint stress (3 times/day and 45 min/each) from E11 to parturition, but not early onset stress from E1 to E11, shortened gestation in pregnant rats, indicating that the restraint stress model is a reliable inducer of PTB among different rodent species. Moreover, while P4 levels decline earlier in both stressed and unstressed wild type mice compared to stressed and unstressed Fkbp5$^{-/-}$ mice, stress induced PTB does not appear to result from a premature decline in serum P4 (FIGS. 9A-9C).

Glucocorticoid therapy in women with anti-phospholipid antibodies and recurrent fetal loss as well as rheumatoid arthritis, results in an increased rate of PTBs. However, no decrease in gestational length was observed in mice exposed to exogenous glucocorticoid therapy. This reflects inhibition of uterine prostaglandin production preventing labor and impairing luteolysis. Thus, the elevated corticosterone levels observed in restrained Fkbp5$^{+/+}$ mice are insufficient to inhibit prostaglandin production, but adequate to induce FKBP51. The current results clearly show that uterine Fkbp5 mRNA and protein levels are prematurely elevated in restrained Fkbp5$^{+/+}$ at E17, whereas this increase occurs physiologically at E19 in unrestrained Fkbp5$^{+/+}$ mice (FIGS. 10A-10B). Thus, in wild type mice restraint stress induces both a 48 h earlier increase in Fkbp5 together with a decrease in uterine Pgr mRNA and protein levels of at E17.25, providing strong evidence that maternal stress initiates PTB by early inhibition of uterine PR signaling (FIGS. 10C-10D).

Other mechanisms to account for the induction of PTB by restraint stress include increased uterine levels of Srd5a1, which metabolizes P4 to 5α-pregnane-3,20-dione and/or decreased expression of 15-hydroxyprostaglandin dehydrogenase (15-Hpgd), the main enzyme that catabolizes prostaglandin E2 and $F_{2\alpha}$. While Srd5a1 deficient mice have only a 27% delivery rate due to impaired cervical ripening, administration of the PR antagonists RU486 or ZK98299 elicits a 100% parturition rate. Moreover, 15-Hpgd hypomorphic mice experience PTB without a decline in serum P4 levels (further evidence that luteolysis is not a cause of labor). However, since we did not detect alteration in the expression of uterine Srd5a1 (FIG. 18C) or 15-Hpgd among these 4 groups, the current results do not support the involvement of Srd5a1 or 15-Hpgd in meditating maternal-stress induced PTB.

Further evidence of early inhibition of uterine progestational signaling resulting from restraint stress is indicated by increased mRNA and protein expression of uterine Akr1c18 at E17.25 in restrained $Fkbp5^{+/+}$ mice. In contrast to wild type mice, Akr1c18 expression was significantly increased without changes in protein expression in restrained vs unrestrained $Fkbp5^{-/-}$ mice at E18.25 (FIGS. 6A-6B). FKBP51 can be an important inducer of AKR1C18 protein expression by enhancing translation and/or reducing degradation of stress induced AKR1C18 protein expression, which require further studies to clarify such mechanisms. Consistent with this enhanced AKR1C18 expression, restraint stress significantly reduces P4 levels in decidual and myometrial cell nuclei in $Fkbp5^{+/+}$ mice at E18.25. This increased P4 metabolism elevates levels of unliganded PR and promotes PR—FKBP51 binding leading to a further inhibition of PR-mediated transcriptional activity, which is supported by the PLA results in humans showing increased PR—FKBP51 interaction in iPTB specimens.

To further confirm this novel FKBP51-mediated mechanism, expression of uterine Oxtr was compared, which is physiologically suppressed by P4 and increased near parturition in all mammalian species, including primates and ruminants, and detected the highest Oxtr levels in the uteri of restrained $Fkbp5^{+/+}$ mice at E18.25, consistent with their earlier delivery. In contrast, $Fkbp5^{-/-}$ mice resist restraint induced labor-related uterine changes by displaying higher Pgr expression and lower Akr1c18 expression together with higher nuclear P4 levels and lower Oxtr levels. Thus, $Fkbp5^{-/-}$ mice are resistant to stress induced functional P4 withdrawal in the uterus.

In conclusion, increased mRNA and protein expression of decidual FKBP5 together with significantly enhanced nuclear FKBP51-PR interaction in decidual cells of iPTB specimens provide a novel mechanism for functional P4 withdrawal as a trigger of iPTB in humans. This study also reports for the first time that $Fkbp5^{-/-}$ mice display a prolonged gestational length, accompanying a slower decline in systemic P4 levels. That functional P4 withdrawal is delayed by Fkbp5 deletion is indicated by lower Oxtr levels at E18.25 in $Fkbp5^{-/-}$ vs. $Fkbp5^{+/+}$ mice. While maternal restraint stress causes PTB in $Fkbp5^{+/+}$ mice by inducing uterine expression of Akr1c18 and Fkbp5 levels, resulting in increased local P4 metabolism and an enhanced FKBP51-PR interaction which blocks PR-mediated transcriptional activity, maternal and fetal Fkbp5 deletion renders mice completely resistant to maternal stress induced PTB. Collectively, these results suggest that FKBP51 plays a pivotal role in both term and preterm parturition and that FKBP51 antagonists may prove to be a novel therapy to prevent iPTB.

```
SEQUENCE
(Amino acid sequence for human FKBP51)
                                              SEQ ID NO: 1
MTTDEGAKNNEESPTATVAEQGEDITSKKDRGVLKIVKRVGNGEETPMI

GDKVYVHYKGKLSNGKKFDSSHDRNEPPFVFSLGKGQVIKAWDIGVATMK

KGEICHLLCKPEYAYGSAGSLPKIPSNATLFFEIELLDFKGEDLFEDGG

IIRRTKRKGEGYSNPNEGATVEIHLEGRCGGRMFDCRDVAFTVGEGEDH

DIPIGIDKALEKMQREEQCILYLGPRYGFGEAGKPKFGIEPNAELIYEV

TLKSFEKAKESWEMDTKEKLEQAAIVKEKGTVYFKGGKYMQAVIQYGKI

VSWLEMEYGLSEKESKASESFLLAAFLNLAMCYLKLREYTKAVECCDKA

LGLDSANEKGLYRRGEAQLLMNEFESAKGDFEKVLEVNPQNKAARLQIS

MCQKKAKEHNERDRRIYANMFKKFAEQDAKEEANKAMGKKTSEGVTNEK

GTDSQAMEEEKPEGHV
```

What is claimed is:

1. A method of delaying or preventing idiopathic preterm birth in a subject, comprising administering to the subject a therapeutically effective amount of a composition comprising, 9 nitro-9E-octadecenoic acid, 10-nitro-9E-octadecenoic acid or a combination thereof.

2. The method of claim 1, wherein the composition comprises 9-nitro-9E-octadecenoic acid.

3. The method of claim 1, wherein the composition comprises 10-nitro-9E-octadecenoic acid.

4. The method of claim 1, wherein the idiopathic preterm birth is caused by stress, depression, or placenta abnormality.

5. The method of claim 1, wherein the composition decreases a level of FKBP51 in a decidual cell.

6. The method of claim 1, wherein the composition inhibits glucocorticoid-induced FKBP51 gene expression in a decidual cell.

7. The method of claim 1, wherein the composition inhibits an interaction between FKBP51 and progesterone receptor.

8. The method of claim 1, wherein a gestational period of the subject is extended as compared to a control.

9. A method of delaying or preventing an idiopathic preterm birth in a subject, comprising
   a) determining whether a biological sample obtained from the subject has an increased level of FKBP51 as compared to a control; and
   b) administering to the subject a therapeutically effective amount of a composition comprising 9-nitro-9E-octadecenoic acid, 10-nitro-9E-octadecenoic acid, or a derivative thereof, or a combination thereof if the biological sample obtained from the subject has an increased level of FKBP51 as compared to the control.

10. The method of claim 9, wherein the composition comprises 9-nitro-9E-octadecenoic acid.

11. The method of claim 9, wherein the composition comprises 10-nitro-9E-octadecenoic acid.

12. The method of claim 9, wherein the composition comprises 15-deoxy-$\Delta$12,14-prostaglandin J2.

13. The method of claim 9, wherein the idiopathic preterm birth is caused by stress, depression, or placenta abnormality.

* * * * *

SEQUENCE LISTING

```
<160> NUMBER OF SEQ ID NOS: 1

<210> SEQ ID NO 1
<211> LENGTH: 457
<212> TYPE: PRT
<213> ORGANISM: Homo sapiens

<400> SEQUENCE: 1

Met Thr Thr Asp Glu Gly Ala Lys Asn Asn Glu Glu Ser Pro Thr Ala
1               5                   10                  15

Thr Val Ala Glu Gln Gly Glu Asp Ile Thr Ser Lys Lys Asp Arg Gly
            20                  25                  30

Val Leu Lys Ile Val Lys Arg Val Gly Asn Gly Glu Glu Thr Pro Met
        35                  40                  45

Ile Gly Asp Lys Val Tyr Val His Tyr Lys Gly Lys Leu Ser Asn Gly
    50                  55                  60

Lys Lys Phe Asp Ser Ser His Asp Arg Asn Glu Pro Phe Val Phe Ser
65                  70                  75                  80

Leu Gly Lys Gly Gln Val Ile Lys Ala Trp Asp Ile Gly Val Ala Thr
```

```
                    85                  90                  95
Met Lys Lys Gly Glu Ile Cys His Leu Leu Cys Lys Pro Glu Tyr Ala
               100                 105                 110

Tyr Gly Ser Ala Gly Ser Leu Pro Lys Ile Pro Ser Asn Ala Thr Leu
               115                 120                 125

Phe Phe Glu Ile Glu Leu Leu Asp Phe Lys Gly Glu Asp Leu Phe Glu
               130                 135                 140

Asp Gly Gly Ile Ile Arg Arg Thr Lys Arg Lys Gly Glu Gly Tyr Ser
145                145                 155                 160

Asn Pro Asn Glu Gly Ala Thr Val Glu Ile His Leu Glu Gly Arg Cys
               165                 170                 175

Gly Gly Arg Met Phe Asp Cys Arg Asp Val Ala Phe Thr Val Gly Glu
               180                 185                 190

Gly Glu Asp His Asp Ile Pro Ile Gly Ile Asp Lys Ala Leu Glu Lys
               195                 200                 205

Met Gln Arg Glu Glu Gln Cys Ile Leu Tyr Leu Gly Pro Arg Tyr Gly
               210                 215                 220

Phe Gly Glu Ala Gly Lys Pro Lys Phe Gly Ile Glu Pro Asn Ala Glu
225                230                 235                 240

Leu Ile Tyr Glu Val Thr Leu Lys Ser Phe Glu Lys Ala Lys Glu Ser
               245                 250                 255

Trp Glu Met Asp Thr Lys Glu Lys Leu Glu Gln Ala Ala Ile Val Lys
               260                 265                 270

Glu Lys Gly Thr Val Tyr Phe Lys Gly Gly Lys Tyr Met Gln Ala Val
               275                 280                 285

Ile Gln Tyr Gly Lys Ile Val Ser Trp Leu Glu Met Glu Tyr Gly Leu
               290                 295                 300

Ser Glu Lys Glu Ser Lys Ala Ser Glu Ser Phe Leu Leu Ala Ala Phe
305                310                 315                 320

Leu Asn Leu Ala Met Cys Tyr Leu Lys Leu Arg Glu Tyr Thr Lys Ala
               325                 330                 335

Val Glu Cys Cys Asp Lys Ala Leu Gly Leu Asp Ser Ala Asn Glu Lys
               340                 345                 350

Gly Leu Tyr Arg Arg Gly Glu Ala Gln Leu Leu Met Asn Glu Phe Glu
               355                 360                 365

Ser Ala Lys Gly Asp Phe Glu Lys Val Leu Glu Val Asn Pro Gln Asn
               370                 375                 380

Lys Ala Ala Arg Leu Gln Ile Ser Met Cys Gln Lys Lys Ala Lys Glu
385                390                 395                 400

His Asn Glu Arg Asp Arg Arg Ile Tyr Ala Asn Met Phe Lys Lys Phe
               405                 410                 415

Ala Glu Gln Asp Ala Lys Glu Glu Ala Asn Lys Ala Met Gly Lys Lys
               420                 425                 430

Thr Ser Glu Gly Val Thr Asn Glu Lys Gly Thr Asp Ser Gln Ala Met
               435                 440                 445

Glu Glu Glu Lys Pro Glu Gly His Val
450                455
```